(12) United States Patent
Bishop et al.

(10) Patent No.: US 9,062,082 B2
(45) Date of Patent: Jun. 23, 2015

(54) D1479 STABLE LIQUID BAP PHOTOINITIATOR AND ITS USE IN RADIATION CURABLE COMPOSITIONS

(75) Inventors: Timothy Edward Bishop, Algonquin, IL (US); Edward Joseph Murphy, Arlington Heights, IL (US); John Edmond Southwell, Glen Ellyn, IL (US); Satyendra Sarmah, Chicago, IL (US); TaiYeon Lee, Crystal Lake, IL (US); John Monroe Zimmerman, Village of Lakewood, IL (US)

(73) Assignee: DSM IP ASSETS B.V., Het Overloon, Heerlen (NL)

( * ) Notice: Subject to any disclaimer, the term of this patent is extended or adjusted under 35 U.S.C. 154(b) by 0 days.

(21) Appl. No.: 13/388,732

(22) PCT Filed: Jun. 21, 2011

(86) PCT No.: PCT/US2011/041158
§ 371 (c)(1),
(2), (4) Date: Feb. 3, 2012

(87) PCT Pub. No.: WO2012/003106
PCT Pub. Date: Jan. 5, 2012

(65) Prior Publication Data
US 2012/0129969 A1 May 24, 2012

Related U.S. Application Data

(60) Provisional application No. 61/359,941, filed on Jun. 30, 2010.

(30) Foreign Application Priority Data

Jul. 16, 2010 (EP) .................................... 10169857

(51) Int. Cl.
| | | |
|---|---|---|
| C08F 2/46 | (2006.01) | |
| C08F 2/50 | (2006.01) | |
| B29C 71/04 | (2006.01) | |
| C08G 61/04 | (2006.01) | |
| C07F 9/50 | (2006.01) | |
| C03C 25/10 | (2006.01) | |
| C03C 25/24 | (2006.01) | |
| C04B 41/00 | (2006.01) | |
| C04B 41/48 | (2006.01) | |
| C04B 41/63 | (2006.01) | |
| C07F 9/53 | (2006.01) | |
| C08F 2/40 | (2006.01) | |
| C09D 133/08 | (2006.01) | |
| C08K 5/50 | (2006.01) | |
| C08F 222/10 | (2006.01) | |

(52) U.S. Cl.
CPC ........... *C07F 9/5036* (2013.01); *C03C 25/1055* (2013.01); *C03C 25/246* (2013.01); *C04B 41/009* (2013.01); *C04B 41/483* (2013.01); *C04B 41/63* (2013.01); *C07F 9/5337* (2013.01); *C08F 2/40* (2013.01); *C08F 2/50* (2013.01); *C08K 5/50* (2013.01); *C09D 133/08* (2013.01); *C08F 222/1006* (2013.01)

(58) Field of Classification Search
USPC .............................. 522/28, 7, 6, 1, 71; 520/1
See application file for complete search history.

(56) References Cited

U.S. PATENT DOCUMENTS

| | | | |
|---|---|---|---|
| 3,668,093 A | 6/1972 | Rettig | |
| 4,737,593 A | 4/1988 | Ellrich et al. | |
| 6,020,528 A | 2/2000 | Leppard et al. | |
| 6,136,880 A | 10/2000 | Snowwhite et al. | |
| 6,359,025 B1 | 3/2002 | Snowwhite et al. | |
| 6,969,733 B2 * | 11/2005 | Wolf et al. ..................... 522/18 | |
| 7,687,657 B2 | 3/2010 | Murer et al. | |
| 2002/0132871 A1 | 9/2002 | Colton et al. | |

(Continued)

FOREIGN PATENT DOCUMENTS

| | | |
|---|---|---|
| EP | 0 184 095 B1 | 6/1986 |
| JP | 1995-278167 A | 10/1995 |

(Continued)

OTHER PUBLICATIONS

European Search Report dated Nov. 14, 2011 issued in European Appln. No. 10169857.9; 10 pages.
Moszner, N. et al. "Synthesis of bis(3-{[2-(allyloxy)ethoxy]methyl}-2,4,6-trimethylbenzoyl)(phenyl)phosphine oxide—a tailormade photoinitiator for dental adhesives", Beilstein Journal of Organic Chemistry, vol. 6, No. 26, Mar. 2010, pp. 1-9. Retrieved from the Internet: URL: http://www.beilstein-journals.org/bjoc/content/pdf/1860-5397-6-26.pdf, XP002614365; 12 pages.
International Search Report and Written Opinion from PCT with Issuance Date of Oct. 20, 2011 in connection with International Application No. PCT/US2011/041158; 6 pages.

(Continued)

*Primary Examiner* — Ling Choi
*Assistant Examiner* — Jessica E Whiteley
(74) *Attorney, Agent, or Firm* — Daniel S. Bujas

(57) ABSTRACT

The invention relates to radiation curable compositions comprising a liquid 0/s(acyl)phosphine photo initiators of formula (I): wherein each of $Ar^1$, $Ar^2$ and $Ar^3$ is independently a substituted or unsubstituted aryl group. The invention also relates to stabilized forms of liquid bis(acyl)phosphines of formula (I) and radiation curable composition comprising said stabilized photoinitiators. The radiation curable compositions are selected from the group consisting of an optical fiber coating composition and a coating composition capable of radiation cure on concrete and a coating composition capable of radiation cure on metal.

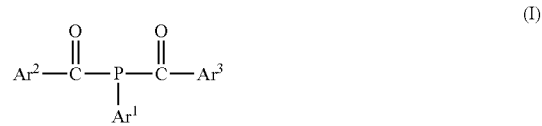

(I)

18 Claims, No Drawings

(56) References Cited

U.S. PATENT DOCUMENTS

| | | |
|---|---|---|
| 2003/0045600 A1 | 3/2003 | Fewkes et al. |
| 2004/0157949 A1 | 8/2004 | Hu et al. |
| 2006/0084716 A1 | 4/2006 | Zahora et al. |

FOREIGN PATENT DOCUMENTS

| | | |
|---|---|---|
| JP | 2003-312148 | * 11/2003 |
| JP | 2008520623 | 6/2008 |
| WO | WO 98/47954 A1 | 10/1998 |
| WO | WO 2005/014606 A1 | 2/2005 |
| WO | WO 2012/003106 A1 | 1/2012 |

OTHER PUBLICATIONS

International Search Report and Written Opinion from PCT with Issuance Date of Jan. 8, 2013 in connection with International Application No. PCT/US2011/041158; 4 pages.

Office Action in related Chinese Application No. 201180003177.1; Date of Issue: Jul. 31, 2013; 15 Pgs.; In Chinese with English Translation.

Response to Office Action in related Chinese Patent Application No. 201180003177.1; filed Nov. 29, 2013; 22 pages.

Office Action in related Korean Patent Application No. 2012-7029914; Date of Issue: Nov. 20, 2013; 18 pages; In Korean with English Translation.

Response to Office Action in related Korean Patent Application No. 2012-7029914; filed Feb. 14, 2014; 42 pages.

Response to Office Action in related European Patent Application No. 11728156.8; filed Mar. 13, 2014; 20 pages.

Office Action in related U.S. Appl. No. 13/802,476; Notification Date: Mar. 12, 2013; 9 pages.

International Search Report for PCT/US2011/041158, mailed Oct. 20, 2011.

Office Action in related Japanese Application No. JP2013534935; Date of Issue: May 27, 2014; 16 Pages; In Japanese with English Translation.

Office Action in related Russian Application No. RU2012148698; Date of Issue: Jun. 25, 2014; 10 Pages, in Russian with English Translation.

* cited by examiner

D1479 STABLE LIQUID BAP PHOTOINITIATOR AND ITS USE IN RADIATION CURABLE COMPOSITIONS

This application is the U.S. national phase of International Application No. PCT/US2011/041158 filed 21 Jun. 2011 which designated the U.S. and claims priority to EP Patent Application No. 10169857.9 filed 16 Jul. 2010 and U.S. Provisional Application No. 61/359,941 filed Jun. 30, 2010, the entire contents of each of which are hereby incorporated by reference.

FIELD OF THE INVENTION

The invention relates to stable liquid bis(acyl)phosphine photoinitiators and radiation curable compositions comprising said photoinitiators.

BACKGROUND OF THE INVENTION

Radiation curable coating compositions are used in many industries including, but not limited to fiber optic materials and coatings for various substrates such as concrete, metal, ceramic, glass, plastic, composites and textiles. Common types of radiation curable compositions are those compositions curable by free radical polymerization. In these compositions, the radiation (e.g., UV radiation) is absorbed by the composition to effect curing or polymerization via the generation of free radicals. The curing of the composition is accomplished by photoinitiators, which absorb the UV energy and react to generate free radicals, which in turn react with double bonds in the composition (e.g., acrylate groups) to form new free radicals (i.e., the initiation step). The newly formed free radicals then react with other double bond centers to polymerize or cure (i.e., solidify) the uncured, liquid composition in the propagation step. Eventually, the polymerization reaction is terminated when the free radicals react with other free radicals instead of reacting with other reactive sites to form new free radicals. This step is aptly referred to as the termination step. In view of the foregoing, it is apparent that the choice of photoinitiator is important to the success of a free radical polymerization process.

A review of photoinitiators for UV curing is disclosed in "A Compilation of Photoinitiators Commercially Available for UV Today" by Dr. Kurt Dietliker of Ciba Specialty Chemicals PLC published by SITA Technology Limited (2002), which is incorporated herein by reference in its entirety. In April 2009, Ciba Holding AG was acquired by BASF.

Radiation-curable compositions are extensively used in the optical fiber industry during the production of optical fibers, ribbons and cables. For example, optical glass fibers are routinely coated with at least two radiation-curable coatings immediately after the glass fiber is manufactured in a draw tower so as to preserve the pristine character of the glass fiber and protect it sufficiently such that it can be collected on a round spool. Immediately after a coating is applied to the fiber, the coating is rapidly cured by exposure to radiation (commonly ultraviolet light). The industry demands faster production speeds and therefore, faster curing coating compositions.

Radiation-curable up-jacketing, matrix and bundling materials can further support and protect the individual strands of coated fiber as individual strands are bundled together into optical fiber ribbons, optical fiber cables and associated structures. In addition, radiation-curable inks can be used to color code individual strands of optical fiber. All of these types of optical fiber-related materials are radiation-curable and can serve as coating and/or cabling materials.

Examples of radiation-curable inner primary coatings are disclosed in U.S. Pat. No. 5,336,563 to Coady et al. and of outer primary coatings (e.g., secondary coatings) in U.S. Pat. No. 4,472,019 to Bishop et al. Additional aspects of optical fiber coating technology are disclosed in, for example, U.S. Pat. No. 5,595,820 to Szum; U.S. Pat. No. 5,199,098 to Nolan et al.; U.S. Pat. No. 4,923,915 to Urruti et al.; U.S. Pat. No. 4,720,529 to Kimura et al.; and U.S. Pat. No. 4,474,830 to Taylor et al., each of which is incorporated herein by reference in their entirety.

The following U.S. patent applications, describing and claiming illustrative radiation curable coating compositions, are incorporated by reference in their entirety: U.S. patent application Ser. No. 11/955,935, filed Dec. 13, 2007, published as US 20080226916 on Sep. 19, 2008; U.S. patent application Ser. No. 11/955,838, filed Dec. 13, 2007, published as US 20080241535 on Oct. 23, 2008; U.S. patent application Ser. No. 11/955,547, filed Dec. 13, 2007, published as US 20080226912 on Sep. 19, 2008; U.S. patent application Ser. No. 11/955,614, filed Dec. 13, 2007, published as US 20080226914 on Sep. 19, 2008; U.S. patent application Ser. No. 11/955,604, filed Dec. 13, 2007, published as US 20080226913 on Sep. 19, 2008; U.S. patent application Ser. No. 11/955,721, filed Dec. 13, 2007, published as US 20080233397 on Sep. 25, 2008; U.S. patent application Ser. No. 11/955,525, filed Dec. 13, 2007, published as US 20080226911 on Sep. 19, 2008; U.S. patent application Ser. No. 11/955,628, filed Dec. 13, 2007, published as US 20080226915 on Sep. 19, 2008; and U.S. patent application Ser. No. 11/955,541, filed Dec. 13, 2007, published as US 20080226909 on Sep. 19, 2008.

Radiation-curable coatings are used as coatings for concrete and metal. UV curable concrete coatings are discussed, for example, in the article, "UV Curable Concrete Coatings" by Jo Ann Arceneaux, Ph.D., Cytec Industries Inc., Smyrna, Ga., presented at the Federation of Societies for Coatings Technology, "Coatings for Concrete Conference: "Coating the World of Concrete," on Feb. 2, 2009 at the Westin Casuarina Las Vegas Hotel in Las Vegas, Nev. and in the article, "Field-Applied, UV-Curable Coatings for Concrete Flooring," by Peter T. Weissman, published in the January/February/March 2009 RADTECH Report.

UVolve® Instant Floor Coatings (available from DSM), are high performance, instant cure coating systems for concrete floors which have the following features and benefits:

virtually instantly curing ability allows for immediate traffic—even forklift;

one-component system with no mixing, with no pot life constraints or wasted product;

the cured coating protects concrete against damage from dirt, wear and chemicals; and cured UVolve® Instant Floor Coatings clean easily—especially forklift tire marks.

The use of radiation curable coatings for concrete floors means that the facility maintenance costs will be lower due to easy clean. UVolve® Instant Floor Coatings have zero VOC, no solvents, and 100% solids. UVolve® Instant Floor Coatings cure to a high gloss, durable finish which exhibits excellent scratch and impact resistance. They are available in both clear and pigmented systems and cure instantly with the use of a UV light machine specifically designed for use with UVolve® Instant Floor Coatings. See: http://www.uvolve-coatings.com/.

The UVaCorr® Corrosion-Resistant UV Coatings for Tube & Pipe (UVaCorr® products are available from DSM), are high performance, radiation curable coating systems used to improve the corrosion resistance of tube and pipe. The UVaCorr® coatings are available as both clear and colored coatings and are used to protect tube and pipe during storage and transport. The UVaCorr® product line, now certified for use in the Venjakob™ Ven Spray Pipe system (trademark of Venjakob), boast several performance advantages over traditional solvent-based and water-borne tube & pipe coatings, including: instant cure for high-speed processing; 100% solid coatings for higher applied coverage and no VOC's; better salt spray resistance for enhanced performance; and smaller equipment footprint with reduced energy requirements. See: http://www.dsm.com/en_US/html/dsmd/uvention_tube.htm To maximize cure speed in an ultraviolet light cure, at least one photoinitiator is required (photoinitiator may be omitted in an electron beam cure). Several photoinitiators can be used to achieve a suitable balance of surface and through cure. For further discussion of the use of more than one photoinitiator see U.S. Pat. Nos. 6,438,306 and 7,276,543. When more than one photoinitiator is present in a radiation curable composition of the invention, conventional classes of photoinitiators have been found to be useful.

Mono-acyl phosphine oxide type photoinitiators can be used such as Lucirin TPO (2,4,6-trimethylbenzoyl)diphenyl phosphine oxide, available commercially from BASF, which exhibits relatively fast cure speed. However, use of commercial Lucirin TPO can cause undesired crystallization effects in coating compositions (e.g., during aging), which can result in inclusions and loss of optical clarity (detected under a light microscope).

Certain photoinitiators are known to cause yellowing, particularly during long term aging of cured compositions under photolytic aging conditions (e.g., UV or fluorescent light). Heat may also induce yellowing. Discoloration in general and yellowing in particular is undesirable and has become anathema in the industry. Hence, a photoinitiator which would provide for lack of harmful crystalline effects and fast cure, but would result in yellowing, would not sufficiently meet the most stringent industry demands.

Attempts have been made to use purified Lucirin TPO, but the purification steps are costly. Other phosphine oxide photoinitiators (e.g., CGI 403, Ciba) can show reduced amounts of harmful crystallization effect, but they may also have slower cure speed. Hence, it is desirable to provide photoinitiators which can provide both fast cure speed and good optical clarity.

Other desirable performance properties for radiation curable media include: being a liquid at ordinary temperatures and having a sufficiently low viscosity to be excellently coated; providing good productivity at a high curing rate; having sufficient strength and superior flexibility; exhibiting very little physical change during temperature changes over a wide range; having superior heat resistance and superior resistance to hydrolysis; showing superior long term reliability with little physical changes over time; showing superior resistance to chemicals such as acids and alkalis; exhibiting low moisture and water absorption; exhibiting superior light resistance showing the least discoloration over time; and exhibiting high resistance to oils. Moreover, an increased demand for processing speed of cured materials makes it necessary for the coating compositions to cure quickly in a stable manner. Thus, a photo-initiator(s) which decomposes fast must be used for the coating materials to cure quickly.

As of the filing date of the instant application, the art is yet to recognize a photoinitiator which provides an excellent balance of all of these critical properties. For example, a large number of phosphine oxide photoinitiators are disclosed in, for example, U.S. Pat. No. 5,218,009 to Rutsch et al. and U.S. Pat. No. 5,534,559 to Leppard et al. However, these patents do not suggest that any particular species of photoinitiators would solve the above-noted problems and provide an excellent balance of properties.

Japanese Patent Application Laid-open No. 190712/1989 discloses a composition comprising an acyl phosphine oxide as a photo-curable resin composition which realizes high productivity in fast curing. However, this composition is not necessarily cured at a high enough rate to sufficiently increase the productivity of optical fibers while maintaining the characteristics required for an optical fiber coating material.

Another composition comprising a bis-acyl phosphine oxide has been proposed in Japanese Patent Application Laid-open No. 259642/1996 as a photo-curable resin composition which shows high productivity by being cured at a high rate. However, the bis-acyl phosphine oxide containing a long chain aliphatic group disclosed in this Japanese Patent Application has a poor solubility in resin compositions, and hence cannot be dissolved in the resin compositions in an amount sufficient to ensure a high cure rate.

U.S. Pat. Nos. 6,136,880 and 6,359,025 and EP Patent Application EP 0975693 to Snowwhite et al. disclose radiation curable coating compositions for optical fiber comprising solid bis-acylphosphine oxide (BAPO) type photoinitiators.

Bis-acylphosphine oxide (i.e., bis(2,4,6-trimethylbenzoyl) phenylphosphine oxide) (BAPO) is a very potent photoinitiator in radiation curable compositions light-induced polymerization of the ethylenically unsaturated compounds. It has a higher extinction coefficient than acyl phosphine oxides such as TPO or TPO-L and thus typically leads to superb photo speed. However, BAPO is a solid having a low solubility in a variety of monomers and oligomers, which limits its use in some applications.

In an attempt to address the shortcomings of solid BAPO, liquid photoinitiator mixtures of BAPO with bis-acylphosphine (BAP) have been reported. For example, see "Liquid Bis-Acylphosphine Oxide (BAPO) Photoinitiators" by C. C. Chiu from Chitec Technology presented at RADTECH 2010 on Monday, May 24, 2010.

In the Chiu presentation, liquid mixtures of BAPO and BAP (collectively known as "LMBAPO") are described. Although the liquid mixture of BAPO and BAP photoinitiators (i.e., LMBAPO) purportedly has film-curing properties similar to solid BAPO, LMBAPO suffers from poor chemical stability, which limits its industrial application.

Thus, there remains an unmet need for photoinitiators suitable for radiation curable compositions exhibiting a balance of the critical performance properties, including existing in a liquid state for radiation curable compositions.

BRIEF SUMMARY OF THE INVENTION

In a first embodiment the invention provides a radiation curable composition, selected from the group consisting of an optical fiber coating composition and a coating composition capable of radiation cure on concrete and a coating composition capable of radiation cure on metal, wherein the composition comprises a liquid bis(acyl)phosphine of formula (I):

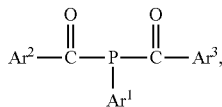  (I)

and at least one free-radical polymerizable component; wherein each of $Ar^1$, $Ar^2$ and $Ar^3$ is independently a substituted or unsubstituted aryl group.

In a second embodiment, the invention provides a radiation curable composition selected from the group consisting of an optical fiber coating composition and a coating composition capable of radiation cure on concrete and a coating composition capable of radiation cure on metal, wherein the composition comprises at least one free-radical polymerizable component and a combination of at least two photoinitiators wherein at least one photoinitiator is bis(2,4,6-trimethylbenzoyl)phenylphosphine and at least one photoinitiator is bis(2,4,6-trimethylbenzoyl)phenylphosphine oxide.

In a third embodiment, the invention provides a liquid bis(acyl)phosphine of formula (I):

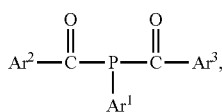  (I)

wherein each of $Ar^1$, $Ar^2$ and $Ar^3$ is independently a substituted or unsubstituted aryl group; and wherein the bis(acyl)phosphine is stabilized with at least one technique selected from the group consisting of low oxygen permeability packaging, refrigeration during shipping and storage and inert gas blanketing.

In a fourth embodiment, the invention provides a liquid bis(acyl)phosphine of formula (I):

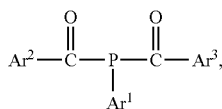  (I)

wherein each of $Ar^1$, $Ar^2$ and $Ar^3$ is independently a substituted or unsubstituted aryl group; and wherein the liquid bis(acyl)phosphine is stabilized as a mixture with one or more compounds selected from the group consisting of a liquid photoinitiator, a solid photoinitiator, a liquid or solid phosphite, a liquid or solid thiophosphinic acid, a liquid or solid phosphine sulfide, a liquid or solid phosphine selenide, a liquid or solid phosphine telluride, a liquid or solid phosphine halogenide, a liquid or solid iminophosphorane, and a liquid or solid dioxaphospholane.

In a sixth embodiment, the invention provides a liquid bis(acyl)phosphine of formula (I):

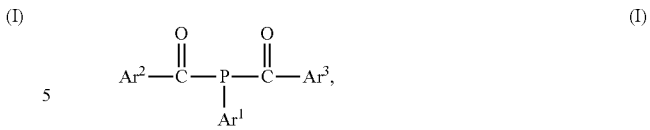  (I)

wherein each of $Ar^1$, $Ar^2$ and $Ar^3$ is independently a substituted or unsubstituted aryl group; and wherein the bis(acyl)phosphine is stabilized as a reaction product with a compound selected from the group consisting of a metal, dodecylsuccinic anhydride, a urea compound, a Lewis acid and a catechol compound.

In a seventh embodiment, the invention provides a radiation curable composition selected from the group consisting of an optical fiber coating composition (preferably selected from the group consisting of a primary coating, a secondary coating, an ink coating, an upjacketing coating, a buffer coating and a matrix coating), and a coating composition capable of radiation cure on concrete and a coating composition capable of radiation cure on metal comprising a liquid bis(acyl)phosphine of formula (I):

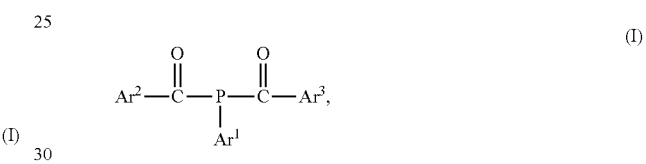  (I)

and at least one free-radical polymerizable component; wherein each of $Ar^1$, $Ar^2$ and $Ar^3$ is independently a substituted or unsubstituted aryl group.

In an eighth embodiment, the invention provides a radiation curable composition of the seventh embodiment, wherein each of $Ar^1$, $Ar^2$ and $Ar^3$ is independently selected from the group consisting of a phenyl group, methylphenyl group, ethylphenyl group, dimethylphenyl group, trialkylphenyl group (preferably a trimethylphenyl group such as a 2,4,6-trimethylphenyl group), isopropylphenyl group, tert-butyl phenyl group, methoxy phenyl group, dimethoxyphenyl group, ethoxy phenyl group, diethoxy phenyl group, isopropoxy phenyl group, thiomethoxy phenyl group, naphthyl group, thiophenyl group and pyridyl group, preferably the phosphine is bis(2,4,6-trimethylbenzoyl)phenylphosphine wherein $Ar^1$ is a phenyl group and each of $Ar^2$ and $Ar^3$ is a 2,4,6-trimethylphenyl group.

In a ninth embodiment, the invention provides a radiation curable composition of the seventh or eighth embodiment, further comprising a bis(acyl)phosphine oxide of formula (II) which is liquid at 20° C.:

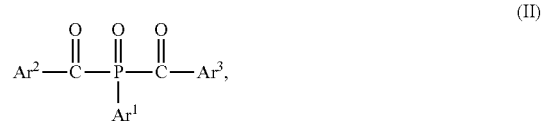  (II)

wherein each of $Ar^1$, $Ar^2$ and $Ar^3$ is independently a substituted or unsubstituted aryl group.

In a tenth embodiment, the invention provides a radiation curable composition of the ninth embodiment, wherein each of $Ar^1$, $Ar^2$ and $Ar^3$ is independently selected from the group consisting of a phenyl group, methylphenyl group, ethylphenyl group, dimethylphenyl group, trialkylphenyl group (preferably a trimethylphenyl group such as a 2,4,6-trimethylphenyl group), isopropylphenyl group, tert-butyl phenyl group, methoxy phenyl group, dimethoxyphenyl group, ethoxy phenyl group, diethoxy phenyl group, isopropoxy phenyl group, thiomethoxy phenyl group, naphthyl group, thiophenyl group and pyridyl group, preferably the phosphine oxide is bis(2,4,6-trimethylbenzoyl)phenylphosphine oxide, wherein $Ar^1$ is a phenyl group and each of $Ar^2$ and $Ar^3$ is a 2,4,6-trimethylphenyl group.

In an eleventh embodiment, the invention provides a radiation curable composition selected from the group consisting of an optical fiber coating composition and a coating composition capable of radiation cure on concrete and a coating composition capable of radiation cure on metal, comprising at least one free-radical polymerizable component and a combination of at least two photoinitiators wherein at least one photoinitiator is bis(2,4,6-trimethylbenzoyl)phenylphosphine that is liquid at 20° C. and at least one photoinitiator is bis(2,4,6-trimethylbenzoyl)phenylphosphine oxide, wherein preferably the combination of bis(acyl)phosphine and bis(acyl)phosphine oxide is liquid at a temperature of about 15° C. or greater,
and wherein preferably the bis(2,4,6-trimethylbenzoyl)phenylphosphine that is liquid at 20° C. and the bis(2,4,6-trimethylbenzoyl)phenylphosphine oxide are present in a ratio of about 1:1 as measured by HPLC.

In a twelfth embodiment, the invention provides a radiation curable composition of any one of the seventh through eleventh embodiments, wherein the composition is curable by UV light generated by a conventional UV light source and/or by a LED light source.

In a thirteenth embodiment, the invention provides a bis(acyl)phosphine of formula (I) that is liquid at 20° C.:

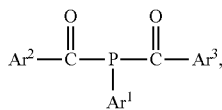

(I)

wherein each of $Ar^1$, $Ar^2$ and $Ar^3$ is independently a substituted or unsubstituted aryl group; and wherein the bis(acyl)phosphine is stabilized with at least one technique selected from the group consisting of low oxygen permeability packaging, refrigeration during shipping and storage and inert gas blanketing.

In a fourteenth embodiment, the invention provides a bis(acyl)phosphine of formula (I) that is liquid at 20° C.:

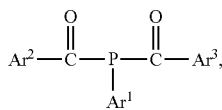

(I)

wherein each of $Ar^1$, $Ar^2$ and $Ar^3$ is independently a substituted or unsubstituted aryl group; and wherein the bis(acyl)phosphine is stabilized as a mixture with one or more compounds selected from the group consisting of a liquid photoinitiator, a solid photoinitiator, a liquid or solid phosphite, a liquid or solid thiophosphinic acid, a liquid or solid phosphine sulfide, a liquid or solid phosphine selenide, a liquid or solid phosphine telluride, a liquid or solid phosphine halogenide, a liquid or solid iminophosphorane, and a liquid or solid dioxaphospholane,
wherein preferably the mixture comprises at least one liquid photoinitiator selected from the group consisting of 2,4,6-(trimethylbenzoyl ethoxy, phenyl phosphine) oxide, diethoxy acetophenone, 2-hydroxy-2-methyl-1-phenyl-propane-1-one, methyl phenylglyoxylate and acrylated benzophenone, wherein preferably the stabilized liquid bis(acyl)phosphine comprises about 25 wt. % to about 75 wt. % of bis(acyl)phosphine.

In a fifteenth embodiment, the invention provides a stabilized liquid bis(acyl)phosphine of the fourteenth embodiment, wherein the bis(acyl)phosphine is stabilized as a mixture with at least one solid photoinitiator selected from the group consisting of 4-methyl benzophenone, p-phenyl benzophenone, 4,4'-bis(dimethylamino)benzophenone, 4-benzoyl-4'-methyl diphenylsulphide, 4,4'-(tetraethyldiamino) benzophenone, 4,4'-(tetraethyldiamino)benzophenone, benzophenone, 2-hydroxy-1-{-4-[4-(2-hydroxy-2-methyl-propionyl)-benzyl]-phenyl}-2-methyl-propan-1-one, 1-hydroxycyclohexyl phenyl ketone, 2,2-dimethoxy-2-phenylacetophenone, 4-(2-hydroxyethoxy)phenyl-(2-propyl)ketone, camphorquinone and 2,4,6-trimethylbenzophenone, wherein preferably the stabilized liquid bis(acyl)phosphine comprises about 25 wt. % to about 75 wt. % of bis(acyl)phosphine, and/or wherein the mixture is preferably an eutectic mixture.

In a sixteenth embodiment, the invention provides a stabilized liquid bis(acyl)phosphine of the fourteenth embodiment, wherein (i) the mixture comprises at least one liquid or solid phosphite of formula (III):

(III)

wherein each of $R^1$, $R^2$ and $R^3$ is independently selected from the group consisting of a $C_1$-$C_{12}$ alkyl group and phenyl group, and wherein the phenyl group is a substituted or unsubstituted phenyl group, wherein preferably each of $R^1$, $R^2$ and $R^3$ is independently an alkylphenyl group, and/or wherein preferably the liquid or solid phosphite is selected from the group consisting of tris(nonylphenyl)phosphite, tributyl phosphite, or mixtures thereof, and/or wherein preferably the mixture is about a 1:1 mixture or less in phosphite;

(ii) the mixture comprises at least one liquid or solid thiophosphinic acid of formula (IV):

(IV)

wherein each of $R^4$ and $R^5$ is independently selected from the group consisting of an alkyl group, an aryl group, an acyl group, and a heteroaryl group, wherein each of $R^4$ and $R^5$ is optionally substituted;

(iii) the mixture comprises at least one liquid or solid phosphine sulfide of formula (V):

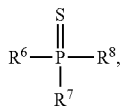

wherein each of $R^6$, $R^7$, and $R^8$ is independently selected from the group consisting of an alkyl group, an aryl group, an acyl group, and a heteroaryl group, wherein each of $R^6$, $R^7$, and $R^8$ is optionally substituted;

(iv) the mixture comprises at least one liquid or solid phosphine selenide of formula (VI):

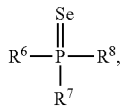

wherein each of $R^1$, $R^2$, and $R^3$ is independently selected from the group consisting of an alkyl group, an aryl group, an acyl group, and a heteroaryl group, wherein each of $R^6$, $R^7$, and $R^8$ is optionally substituted;

(v) the mixture comprises at least one liquid or solid phosphine telluride of formula (VII):

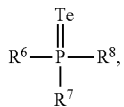

wherein each of $R^6$, $R^7$, $R^8$ is independently selected from the group consisting of an alkyl group, an aryl group, an acyl group, and a heteroaryl group, wherein each of $R^6$, $R^7$, and $R^8$ is optionally substituted;

(vi) the mixture comprises at least one liquid or solid phosphine halogenide of formula (VIII):

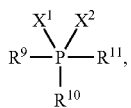

wherein each of $R^9$, $R^{10}$, and $R^{11}$ is independently selected from the group consisting of an alkyl group, an aryl group, an acyl group, and a heteroaryl group, wherein each of $X^1$ and $X^2$ is independently a halogen, and wherein each of $R^9$, $R^{10}$, and $R^{11}$ is optionally substituted;

(vii) the mixture comprises at least one liquid or solid iminophosphorane of formula (IX):

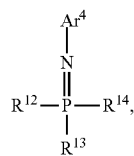

wherein each of $R^{12}$, $R^{13}$, and $R^{14}$ is independently selected from the group consisting of an alkyl group, an aryl group, an acyl group, and a heteroaryl group, wherein $Ar^4$ is an aryl group, and wherein each of $R^{12}$, $R^{13}$, $R^{14}$, and $Ar^4$ is optionally substituted; or (viii) the mixture comprises at least one liquid or solid dioxaphospholane of formula (X):

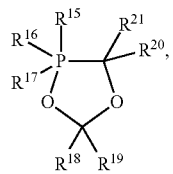

wherein each of $R^{15}$, $R^{16}$, $R^{17}$, $R^{18}$, $R^{19}$, $R^{20}$, and $R^{21}$ is independently selected from the group consisting of an alkyl group, an aryl group, an acyl group, and a heteroaryl group and wherein each of $R^{15}$, $R^{16}$, $R^{18}$, $R^{19}$, $R^{20}$, and $R^{21}$ is optionally substituted.

In a seventeenth embodiment, the invention provides a bis(acyl)phosphine of formula (I) that is liquid at 20° C.:

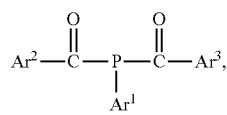

wherein each of $Ar^1$, $Ar^2$ and $Ar^3$ is independently a substituted or unsubstituted aryl group; and wherein the bis(acyl)phosphine is stabilized as a reaction product with a compound selected from the group consisting of a metal, dodecylsuccinic anhydride, a urea compound, a Lewis acid (preferably selected from the group consisting of supramolecular polymers, imidazole derivatives and guanidine derivatives) and a catechol compound.

In an eighteenth embodiment, the invention provides a bis(acyl)phosphine of the seventeenth embodiment, wherein the metal is a transition metal or wherein the metal is selected from the group consisting of vanadium (V), iron (Fe), Indium (In), thorium (Th), mercury (Hg), copper (Cu), nickel (Ni), yttrium (Y), lead (Pb), zinc (Zn), cadmium (Cd), cobalt (Co), manganese (Mn), calcium (Ca), magnesium (Mg), strontium (Sr), barium (Ba), zirconium (Zr), titanium (Ti), chromium (Cr), rubidium (Rb), molybdenum (Mo), ruthenium (Ru), palladium (Pd), silver (Ag), cadmium (Cd), tin (Sn), antimony (Sb), barium (Ba), tungsten (W), platinum (Pt), gold (Au), bismuth (Bi) and beryllium (Be), wherein preferably the stabilized liquid bis(acyl)phosphine has a formula (XI) or formula (XII):

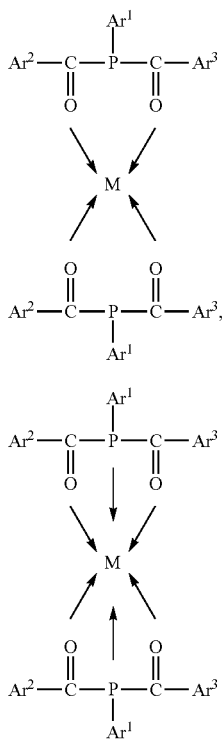

(XI)

(XII)

wherein each of $Ar^1$, $Ar^2$ and $Ar^3$ is independently a substituted or unsubstituted aryl group, and wherein M is a metal.

In a nineteenth embodiment, the invention provides a stabilized liquid bis(acyl)phosphine of the seventeenth embodiment, having formula (XIII) or formula (XIV):

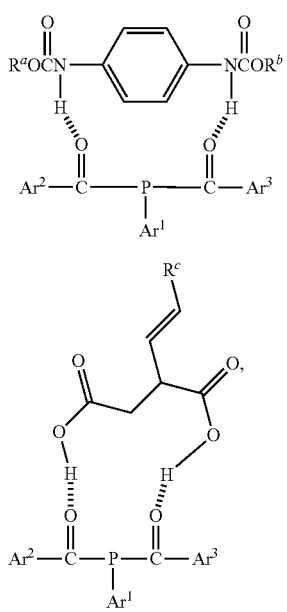

(XIII)

(XIV)

wherein each of $Ar^1$, $Ar^2$ and $Ar^3$ is independently a substituted or unsubstituted aryl group; and wherein each of $R^a$, $R^b$ and $R^c$, is independently selected from the group consisting of hydrogen, an alkyl group and a substituted alkyl group, wherein the alkyl group and substituted alkyl group are optionally substituted.

In a twentieth embodiment, the invention provides a stabilized liquid bis(acyl)phosphine of any one of the thirteenth through nineteenth embodiments, wherein each of $Ar^1$, $Ar^2$ and $Ar^3$ is independently selected from the group consisting of a phenyl group, methylphenyl group, ethylphenyl group, dimethylphenyl group, trialkylphenyl group (preferably a trimethylphenyl group such as a 2,4,6-trimethylphenyl group), isopropylphenyl group, tert-butyl phenyl group, methoxy phenyl group, dimethoxyphenyl group, ethoxy phenyl group, diethoxy phenyl group, isopropoxy phenyl group, thiomethoxy phenyl group, naphthyl group, thiophenyl group and pyridyl group, wherein preferably the stabilized phosphine is stabilized liquid bis(2,4,6-trimethylbenzoyl)phenylphosphine, wherein $Ar^1$ is a phenyl group and each of $Ar^2$ and $Ar^3$ is a 2,4,6-trimethylphenyl group.

In a twenty-first embodiment, the invention provides a radiation curable composition, preferably selected from the group consisting of an optical fiber coating composition (preferably selected from the group consisting of a primary coating, a secondary coating, an ink coating, an upjacketing coating, a buffer coating and a matrix coating), and a coating composition capable of radiation cure on concrete and a coating composition capable of radiation cure on metal, said composition comprising the stabilized liquid bis(acyl)phosphine of any one of the thirteenth through nineteenth embodiments and at least one free-radical polymerizable component.

In a twenty-second embodiment, the invention provides a radiation curable composition of the twenty-first embodiment, wherein said composition is a liquid at 20° C.

In a twenty-third embodiment, the invention provides a radiation curable composition of the twenty-first or twenty-second embodiment, wherein the composition is curable by UV light generated by a conventional UV light source and/or by light generated by a LED light source.

DETAILED DESCRIPTION OF THE INVENTION

Throughout this application, the following abbreviations have the indicated meanings:

| | |
|---|---|
| A-189 | γ-mercaptopropyl trimethoxy silane available from Momentive |
| ACCLAIM 4200 | polypropylene glycol, MW = 4200, available from Bayer |
| BAP | bis(acyl)phosphine |
| BAPO | bis(acyl)phosphine oxide |
| BHT | 2,6-di-tert-butyl-4-methylphenol, available from Fitz Chem. |
| DBTDL | dibutyl tin dilaurate, available from OMG Americas |
| HEA | hydroxyethyl acrylate, available from BASF |
| IRGACURE 819 | bis(2,4,6-trimethylbenzoyl)phenylphosphine oxide, available from Ciba Specialty Chemicals(now owned by BASF) |
| IRGANOX 1035 | thiodiethylene bis(3,5-di-tert-butyl-4-hydroxyphenyl)propionate), available from Ciba, Inc. (now owned by BASF) |
| LMBAPO | A mixture of bis(acyl)phosphine oxide and bis(acyl)phosphine |
| MONDUR TDS | 100% 2,4-isomer of toluene diisocyanate, available from Bayer |
| SR-339A | 2-phenoxyethyl acrylate |
| SR-349 | ethoxylated (3) bisphenol A diacrylate, available from Sartomer |
| SR-504D | ethoxylated nonyl phenol acrylate, available from Sartomer |
| TINUVIN 123 | bis(1-octyloxy-2,2,6,6-tetramethyl-4-piperidyl)sebacate, available from Ciba, Inc. (now owned by BASF) |
| TPO | 2,4,6-trimethylbenzoyl diphenyl phosphine oxide |

| | |
|---|---|
| TPO-L | 2,4,6-(trimethylbenzoyl ethoxy, phenyl phosphine)oxide |

In this specification a number of terms are used which are well known to a skilled addressee. Nevertheless for the purposes of clarity a number of terms will be defined.

As used herein, the term unsubstituted means that there is no substituent or that the only substituents are hydrogen.

"Alkyl" as a group or part of a group refers to a straight or branched aliphatic hydrocarbon group, preferably a $C_1$-$C_{18}$ alkyl, more preferably $C_1$-$C_{12}$ alkyl, yet more preferably $C_1$-$C_9$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Acyl" means an alkyl-CO— group or an aryl-CO— group in which the alkyl or aryl group is as described herein, examples of acyl include acetyl and benzoyl. The alkyl group is preferably a $C_1$-$C_6$ alkyl or optionally substituted aryl group. The group may be a terminal group or a bridging group.

"Alkoxy" refers to an —O-alkyl group in which alkyl is defined herein. Preferably the alkoxy is a $C_1$-$C_6$alkoxy. Examples include, but are not limited to, methoxy and ethoxy. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_5$-$C_7$ cycloalkyl or $C_5$-$C_7$ cycloalkenyl group are fused together to form a cyclic structure, such as tetrahydronaphthyl, indenyl or indanyl. The group may be a terminal group or a bridging group.

"Halogen" represents chlorine, fluorine, bromine or iodine.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group, may be a terminal group or a bridging group. As used herein, reference to the normal chain when used in the context of a bridging group refers to the direct chain of atoms linking the two terminal positions of the bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulfur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

The invention provides a radiation curable composition, radiation curable optical fiber coating compositions and radiation coating compositions capable of radiation cure on concrete or radiation cure on metal. The radiation curable compositions of the invention comprise a liquid bis(acyl) phosphine of formula (I) as a photoinitiator:

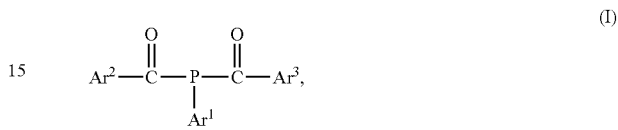

and at least one free-radical polymerizable component.

Liquid (i.e. liquid at 20° C.) bis(2,4,6-trimethylbenzoyl) phenylphosphine, that is, a compound of formula (I) wherein $Ar^1$ is phenyl, $Ar^2$ and $Ar^3$ are each 2,4,6-trimethylphenyl has been reported as a highly unstable compound which readily oxidizes to bis(2,4,6-trimethylbenzoyl)phenylphosphine oxide. Liquid bis(2,4,6-trimethylbenzoyl)phenylphosphine reportedly can not be isolated as a pure compound due to its inherent chemical instability. Accordingly, it is isolated as a mixture of the phosphine and phosphine oxide. A 2:1 mixture of the phosphine and phosphine oxide is reportedly a liquid with improved stability compared to the phosphine compound. The photospeed properties of the 2:1 mixture in cured films has been reported. Heretofore, a radiation curable optical fiber coating composition or radiation coating compositions capable of radiation cure on concrete or radiation cure on metal comprising a bis(acyl)phosphine of formula (I) has not been reported.

Applicants have discovered that liquid bis(acyl)phosphine photoinitiators of formula (I) can be incorporated into radiation curable optical fiber coating compositions and radiation curable coating compositions capable of radiation cure on concrete or radiation cure on metal.

Bis(acyl)phosphines of formula (I) that are liquid at 20° C. comprise aryl groups (i.e., $Ar^1$, $Ar^2$ and $Ar^3$). In keeping with the invention, each of $Ar^1$, $Ar^2$ and $Ar^3$ of the bis(acyl)phosphine of formula (I) independently can be substituted or unsubstituted.

The bis(acyl)phosphine photoinitiators of formula (I) are liquid at 20° C., thereby avoiding the drawbacks of solid photoinitiators (e.g., BAPO sold commercially as IRGACURE® 819 by Ciba (now owned by BASF)). For example, liquid bis(acyl)phosphine photoinitiators of the invention exhibit ease of handling, good compatibility with resins and pigments, lack of crystallization problems and no fine dust hazards.

By way of nonlimiting example, when any of the aryl groups is a phenyl group(s), the phenyl group(s) can be mono-, di-, tri-, tetra- or penta-substituted, as appropriate. Moreover, the phenyl group(s), are optionally substituted in any suitable position, for example, ortho-, meta-, para-substituted. By way of further example, when an aryl group is phenyl, the phenyl group can have the following structure:

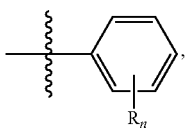

wherein each R can be independently any substituent selected from the group consisting of hydrogen, $C_1$-$C_6$ alkyl, $C_1$-$C_6$ alkylaryl, $C_1$-$C_6$ alkoxy, $C_5$-$C_{10}$ aryl, alkylaryloxy, alkyloxyaryl, heteroalkyl, heteroaryl, heteroalkoxy and halogen, and wherein n represents the number of R substituents on the phenyl ring and n is an integer from 0-5 (i.e., the maximum number of substitution sites on the phenyl group).

The skilled artisan recognizes that the maximum number of substituents (i.e., maximum value of n) varies with the aryl group.

In embodiments wherein an aryl group(s) is substituted, each substituent can be independently any substituent selected from the group consisting of hydrogen, $C_1$-$C_6$ alkyl, $C_1$-$C_6$ alkylaryl, $C_1$-$C_6$ alkoxy, $C_5$-$C_{10}$ aryl, alkylaryloxy, alkyloxyaryl, heteroalkyl, heteroaryl and heteroalkoxy, and n is from 1 to the maximum to number of substitution sites, as appropriate.

By way of further illustration, suitable substituents include electron withdrawing groups including, but not limited to halogens, nitrile groups and carbonyl groups. Moreover, suitable substituents also include electron releasing groups including, but not limited to hydroxy groups and amino groups, including substituted amino groups (e.g., —NHR and —NHR$_2$ wherein R is an alkyl group).

In addition, $Ar^1$, $Ar^2$ and $Ar^3$ can include aryl groups which include hetero atoms such as an oxygen atom, a sulfur atom, a halogen atom or a nitrogen atom (i.e., heteroaryl groups).

In an embodiment, each of $Ar^1$, $Ar^2$ and $Ar^3$ is selected from the group consisting of phenyl group, methylphenyl group, ethylphenyl group, dimethylphenyl group, trialkylphenyl group, isopropylphenyl group, tert-butyl phenyl group, methoxy phenyl group, dimethoxyphenyl group, ethoxy phenyl group, diethoxy phenyl group, isopropoxy phenyl group, thiomethoxy phenyl group, naphthyl group, thiophenyl group and pyridyl group.

In an embodiment, the trialkyphenyl group is a trimethylphenyl group.

In another embodiment, the trimethylphenyl group is a 2,4,6-trimethylphenyl group.

In an embodiment, the radiation curable coating compositions of the invention comprise liquid bis(2,4,6-trimethylbenzoyl)phenylphosphine wherein $Ar^1$ is a phenyl group and each of $Ar^2$ and $Ar^3$ is a 2,4,6-trimethylphenyl group.

The radiation curable compositions of the invention comprise at least one free-radical polymerizable component. The radiation curable compositions of the invention typically comprise an acrylate group as a free-radical polymerizable component. Other suitable free-radical polymerizable components include, for example, methacrylate, acrylamide, methylacrylamide, vinyl amide, vinyl ether groups and other ethylenic unsaturated moieties known to the skilled artisan.

In an embodiment, the invention provides a radiation curable optical fiber coating composition comprising a liquid bis(acyl)phosphine of formula (I) and at least one free-radical polymerizable component. The optical fiber coating composition of the invention can be any suitable optical fiber coating composition. In an embodiment the optical fiber coating composition is selected from the group consisting of a primary coating, a secondary coating, an ink coating, an upjacketing coating, a buffer coating and a matrix coating.

In another embodiment, the invention provides a radiation curable coating composition capable of radiation cure on concrete comprising a liquid bis(acyl)phosphine of formula (I) and at least one free-radical polymerizable component.

Commercially available, radiation curable coating compositions for concrete are known to the skilled artisan. For example, see http://www.uvolvecoatings.com/.

In another embodiment, the invention provides a radiation curable coating composition capable of radiation cure on metal comprising a liquid bis(acyl)phosphine of formula (I) and at least one free-radical polymerizable component.

Commercially available, radiation curable coating compositions for metal are known to the skilled artisan. For example, see http://www.dsm.com/en_US/html/dsmd/uvention_tube.htm.

In an embodiment, the invention provides a radiation curable optical fiber coating composition or radiation coating compositions capable of radiation cure on concrete or radiation cure on metal wherein the compositions comprise a liquid bis(acyl)phosphine of formula (I) as described herein, and a liquid bis(acyl)phosphine oxide of formula (II) and at least one free-radical polymerizable component:

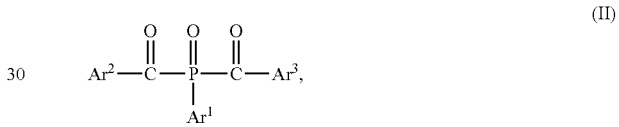

(II)

wherein each of $Ar^1$, $Ar^2$ and $Ar^3$ of formula (II) has the meaning of $Ar^1$, $Ar^2$ and $Ar^3$ of bis(acyl)phosphine of formula (I).

In an embodiment, the invention provides a radiation curable optical fiber coating composition, or a radiation curable coating composition capable of radiation cure on concrete or a radiation curable coating composition capable of radiation cure on metal wherein the compositions comprise or consist of at least one free-radical polymerizable component and a combination of at least two photoinitiators wherein at least one photoinitiator is bis(2,4,6-trimethylbenzoyl)phenylphosphine and at least one photoinitiator is bis(2,4,6-trimethylbenzoyl)phenylphosphine oxide.

In keeping with an aspect of the invention, the radiation curable composition is a liquid. In an embodiment the combination of bis(2,4,6-trimethylbenzoyl)phenylphosphine and bis(2,4,6-trimethylbenzoyl)phenylphosphine oxide is a liquid at a temperature greater than about 15° C.

As used herein, the term "about" means ±10% of the stated value.

In an embodiment, the liquid bis(2,4,6-trimethylbenzoyl)phenylphosphine and bis(2,4,6-trimethylbenzoyl)phenylphosphine oxide are present in a ratio of about 1:1 as measured by HPLC. In another embodiment, the ratio is about 2:1 phosphine to phosphine oxide as measured by HPLC.

The radiation curable coating compositions of the invention are designed to be cured by conventional UV lights. However, should it be desirable to cure the instant claimed coating compositions using LED light, Applicants have designed coating compositions which are curable by light generated by a LED source.

The use of ultraviolet mercury arc lamps to emit ultraviolet light suitable to cure radiation curable coatings applied to optical fiber is well known. Ultraviolet arc lamps emit light by using an electric arc to excite mercury that resides inside an inert gas (e.g., argon) environment to generate ultraviolet light which effectuates curing. Alternatively, microwave energy can also be used to excite mercury lamps in an inert gas medium to generate the ultraviolet light. Throughout this patent application, arc excited and microwave excited mercury lamp, plus various additives (ferrous metal, gallium, etc.) modified forms of these mercury lamps are identified as mercury lamps.

However, the use of ultraviolet mercury lamps as a radiation source suffers from several disadvantages including environmental concerns from mercury and the generation of ozone as a by-product. Further, mercury lamps typically have lower energy conversion ratio, require warm-up time, generate heat during operation, and consume a large amount of energy when compared with LED. In the production of coated optical fiber, the heat generated by the UV mercury lamps can negatively impact the liquid coating in that if the coating is not formulated to avoid the presence of volatiles, those volatiles may be excited and deposit upon the quartz tube surface, blocking the UV rays from irradiating the liquid coating on the glass fiber which inhibits the curing of the liquid coating to a solid. In addition, mercury lamps are characterized by a broad spectral output, in addition to the UV radiation, much of which is not useful for curing and can damage substrates and presents hazards to personnel. Accordingly, alternative radiation sources are being investigated.

Light emitting diodes (LEDs) are semiconductor devices which use the phenomenon of electroluminescence to generate light. LEDs consist of a semiconducting material doped with impurities to create a p-n junction capable of emitting tight as positive holes join with negative electrons when voltage is applied. The wavelength of emitted light is determined by the materials used in the active region of the semiconductor. Typical materials used in semiconductors of LEDs include, for example, elements from Groups 13 (III) and 15 (V) of the periodic table. These semiconductors are referred to as III-V semiconductors and include, for example, GaAs, GaP, GaAsP, AlGaAs, InGaAsP, AlGaInP and InGaN semiconductors. Other examples of semiconductors used in LEDs include compounds from Group 14 (IV-IV semiconductor) and Group 12-16 (II-VI). The choice of materials is based on multiple factors including desired wavelength of emission, performance parameters and cost.

Early LEDs used gallium arsenide (GaAs) to emit infrared (IR) radiation and low intensity red light. Advances in materials science have led to the development of LEDs capable of emitting light with higher intensity and shorter wavelengths, including other colors of visible light and UV light. It is possible to create LEDs that emit light anywhere from a low of about 100 nm to a high of about 900 nm. Currently, known LED UV light sources emit light at wavelengths between about 300 and about 475 nm, with 365 nm, 390 nm and 395 nm being common peak spectral outputs. See textbook, "Light-Emitting Diodes" by E. Fred Schubert, $2^{nd}$ Edition, © E. Fred Schubert 2006, published by Cambridge University Press. When using LED lamps for curing coating compositions, the photoinitiator is the coating composition is selected to be responsive to the wavelength of light emitted by the LED lamp.

LED lamps offer advantages over mercury lamps in curing applications. For example, LED lamps do not use mercury to generate UV light and are typically less bulky than mercury UV arc lamps. In addition, LED lamps are instant on/off sources requiring no warm-up time, which contributes to LED lamps' low energy consumption. LED lamps also generate much less heat, with higher energy conversion efficiency, have longer lamp lifetimes, and are essentially monochromatic emitting a desired wavelength of light which is governed by the choice of semiconductor materials employed in the LED.

Several manufacturers offer LED lamps for commercial curing applications. For example, Phoseon Technology, Summit UV, Honle UV America, Inc., IST Metz GmbH, Jenton International Ltd., Lumios Solutions Ltd., Solid UV Inc., Seoul Optodevice Co., Ltd, Spectronics Corporation, Luminus Devices Inc., and Clearstone Technologies, are some of the manufacturers currently offering LED lamps for curing ink-jet printing compositions, PVC floor coating compositions, metal coating compositions, plastic coating composition and adhesive compositions.

LED curing of radiation curable coatings for optical fiber is described and claimed in U.S. Provisional Patent Application 61/287,567, filed 17 Dec. 2009, entitled, D1429 "BT LED Curing of Radiation Curable Optical Fiber Coating Compositions", which is incorporated herein by reference, in its entirety.

In an embodiment, the invention provides a radiation curable composition wherein the composition is curable by UV light generated by a conventional UV light source.

In another embodiment, the invention provides a radiation curable composition wherein the composition is curable by light generated by a LED light source.

In an embodiment, the present invention provides a radiation curable optical fiber coating composition. As used herein, "optical fiber" coating refers to primary coatings (i.e., inner primary coatings), secondary coatings (i.e., outer primary coatings), ink coatings, up-jacketing coatings, matrix coatings and cabling (bundling) materials. Optical fiber coating compositions of the invention comprise at least one radiation-curable oligomer, at least one radiation-curable monomer diluent, at least one bis(acyl)phosphine photoinitiator of formula (I), and additives. The details of radiation curable optical fiber coating compositions are described in, for example, U.S. Pat. No. 6,136,880 to Snowwhite et al., which is incorporated herein by reference in its entirety.

Examples of radiation-curable inner primary coatings are disclosed in U.S. Pat. No. 5,336,563 to Coady et al. and of outer primary coatings (e.g., secondary coatings) in U.S. Pat. No. 4,472,019 to Bishop et al. Additional aspects of optical fiber coating technology are disclosed in, for example, U.S. Pat. No. 5,595,820 to Szum; U.S. Pat. No. 5,199,098 to Nolan et al.; U.S. Pat. No. 4,923,915 to Urruti et al.; U.S. Pat. No. 4,720,529 to Kimura et al.; and U.S. Pat. No. 4,474,830 to Taylor et al., each of which is incorporated herein by reference in their entirety.

The article, "UV-CURED POLYURETHANE-ACRYLIC COMPOSITIONS AS HARD EXTERNAL LAYERS OF TWO-LAYER PROTECTIVE COATINGS FOR OPTICAL FIBRES", authored by W. Podkoscielny and B. Tarasiuk, Polim. Tworz. Wielk, Vol. 41, Nos. 7/8, p. 448-55, 1996, NDN-131-0123-9398-2, describes studies of the optimization of synthesis of UV-cured urethane-acrylic oligomers and their use as hard protective coatings for optical fibers. Polish-made oligoetherols, diethylene glycol, toluene diisocyanate (Izocyn T-80) and isophorone diisocyanate in addition to hydroxyethyl and hydroxypropyl(meth)acrylates were used for the synthesis. Active diluents (butyl acrylate, 2-ethylhexyl acrylate and 1,4-butanediol acrylate or mixtures of these) and 2,2-dimethoxy-2-phenylacetophenone as a photoinitiator were added to these urethane-acrylic oligomers which had polymerization-active double bonds. The compositions were UV-irradiated in an oxygen-free atmosphere. IR spectra of the compositions were recorded, and some physical and chemical and mechanical properties (density, molecular weight, viscosity as a function of temperature, refractive index, gel content, glass transition temperature, Shore hardness, Young's modulus, tensile strength, elongation at break, heat resistance and water vapor diffusion coefficient) were determined before and after curing. The article, "PROPERTIES OF ULTRAVIOLET CURABLE POLYURETHANE-ACRYLATES", authored by M. Koshiba; K. K. S. Hwang; S. K. Foley; D. J. Yarusso; and S. L. Cooper; published in J. Mat. Sci., 17, No. 5, May 1982, p. 1447-58; NDN-131-0063-1179-2; described a study that was made of the relationship between the chemical structure and physical properties of UV cured polyurethane-acrylates based on isophorone diisocyanate and TDI. The two systems were prepared with varying soft segment molecular weight and cross linking agent content. Dynamic mechanical test results showed that one- or two-phase materials might be obtained, depending on soft segment molecular weight. As the latter increased, the polyol Tg shifted to lower temperatures. Increasing using either N-vinyl pyrrolidone (NVP) or polyethylene glycol diacrylate (PEGDA) caused an increase in Young's modulus and ultimate tensile strength. NVP cross linking increased toughness in the two-phase materials and shifted the high temperature Tg peak to higher temperatures, but PEGDA did not have these effects. Tensile properties of the two systems were generally similar.

Typically in the manufacture of radiation curable coatings for use on optical fiber, isocyanates are used to make urethane oligomers. In many references, including U.S. Pat. No. 7,135, 229, "RADIATION-CURABLE COATING COMPOSITION", Issued Nov. 14, 2006, assigned to DSM IP Assets B.V., column 7, lines 10-32 the following teaching is provided to guide the person of ordinary skill in the art how to synthesize urethane oligomer: polyisocyanates suitable for use in making compositions of the present invention can be aliphatic, cycloaliphatic or aromatic and include diisocyanates, such as 2,4-toluene diisocyanate, 2,6-toluene diisocyanate, 1,3-xylene diisocyanate, 1,4-xylylene diisocyanate, 1,5-naphthalene diisocyanate, m-phenylene diisocyanate, p-phenylene diisocyanate, 3,3'-dimethyl-4,4'-diphenylmethane diisocyanate, 4,4'-diphenylmethane diisocyanate, 3,3'-dimethylphenylene diisocyanate, 4,4'-biphenylene diisocyanate, 1,6-hexane diisocyanate, isophorone diisocyanate, methylenebis(4-cyclohexyl)isocyanate, 2,2,4-trimethylhexamethylene diisocyanate, bis(2-isocyanate-ethyl)fumarate, 6-isopropyl-1,3-phenyl diisocyanate, 4-diphenylpropane diisocyanate, lysine diisocyanate, hydrogenated diphenylmethane diisocyanate, hydrogenated xylylene diisocyanate, tetramethylxylylene diisocyanate and 2,5(or 6)-bis(isocyanatomethyl)-bicyclo[2.2.1]heptane. Among these diisocyanates, 2,4-toluene diisocyanate, isophorone diisocyanate, xylene diisocyanate, and methylenebis(4-cyclohexylisocyanate) are particularly preferred. These diisocyanate compounds are used either individually or in combination of two or more.

In many of these compositions, use is made of a urethane oligomer having reactive termini and a polymer backbone. Further, the compositions generally comprise reactive diluents, photoinitiators to render the compositions UV-curable, and other suitable additives.

Published PCT Patent Application WO 2005/026228 A1, published Sep. 17, 2004, "Curable Liquid Resin Composition", with named inventors Sugimoto, Kamo, Shigemoto, Komiya and Steeman describes and claims a curable liquid resin composition comprising: (A) a urethane (meth)acrylate having a structure originating from a polyol and a number average molecular weight of 800 g/mol or more, but less than 6000 g/mol, and (B) a urethane (meth)acrylate having a structure originating from a polyol and a number average molecular weight of 6000 g/mol or more, but less than 20,000 g/mol, wherein the total amount of the component (A) and component (B) is 20-95 wt % of the curable liquid resin composition and the content of the component (B) is 0.1-30 wt % of the total of the component (A) and component (B).

Many materials have been suggested for use as the polymer backbone for the urethane oligomer. For example, polyols such as hydrocarbon polyols, polyether polyols, polycarbonate polyols and polyester polyols have been used in urethane oligomers. Polyester polyols are particularly attractive because of their commercial availability, oxidative stability and versatility to tailor the characteristics of the coating by tailoring the backbone. The use of polyester polyols as the backbone polymer in a urethane acrylate oligomer is described, for example, in U.S. Pat. Nos. 5,146,531, 6,023, 547, 6,584,263, 6,707,977, 6,775,451 and 6,862,392, as well as European Patent 539 030 A.

Concern over the cost, use and handling of urethane precursors has lead to the use of urethane-free oligomers in coating compositions. For example, urethane-free polyester acrylate oligomers have been used in radiation-curable coating compositions for optical glass fibers. Japanese Patent 57-092552 (Nitto Electric) discloses all optical glass fiber coating material comprising a polyester di(meth)acrylate where the polyester backbone has an average molecular weight of 300 or more. German Patent Application 04 12 68 60 A1 (Bayer) discloses a matrix material for a three-fiber ribbon consisting of a polyester acrylate oligomer, 2-(N-butyl-carbamyl)ethylacrylate as reactive diluent and 2-hydroxy-2-methyl-1-phenyl-propan-1-one as photoinitiator. Japanese Patent Application No. 10-243227 (Publication No. 2000-072821) discloses a liquid curable resin composition comprising a polyester acrylate oligomer which consists of a polyether diol end-capped with two diackls or anhydrides and terminated with hydroxy ethyl acrylate. U.S. Pat. No. 6,714, 712 B2 discloses a radiation curable coating composition comprising a polyester and/or alkyd (meth)acrylate oligomer comprising a polyacid residue or an anhydride thereof, optionally a reactive diluent, and optionally a photoinitiator. Also, Mark D. Soucek and Aaron H. Johnson disclose the use of hexahydrophthalic acid for hydrolytic resistance in "New Intramolecular Effect Observed for Polyesters: An Anomeric Effect," JCT Research, Vol. 1, No. 2, p. 111 (April 2004).

The radiation curable compositions of the invention can comprise more than one photoinitiator. In addition to the liquid bis(acyl)phosphines of formula (I), the radiation curable compositions can comprise any suitable photoinitiator. Illustrative bis(acyl)phosphine oxides of formula (II) which can be included are, for example, bis-(2,4,6-trimethylbenzoyl)-phenylphosphine oxide (hereinafter abbreviated as "BTBPO"); bis-(2,6-dimethylbenzoyl)-phenylphosphine oxide; bis(benzoyl)phenylphosphine oxide; bis-(2,6-dimethoxybenzoyl) phenylphosphine oxide; and bisbenzoyl (2,4,6-trimethyl)phenylphosphine oxide.

Photoinitiators other than those represented by formula (I) or formula (II) can be jointly used as a photoinitiator in the liquid curable resin composition of the present invention. Also, a photosensitizer may be added as required. Suitable photosensitizers are known to the skilled artisan.

Examples of the photoinitiator which can be jointly used include 1-hydroxycyclohexyl phenyl ketone, 2,2-dimethoxy-2-phenylacetophenone, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, Michler's ketone, benzoinpropyl ether, benzomethyl ether, benzyldimethyl ketal, 1-(4-isopropylphenyl)-2-hydroxy-2-methylpropane-1-one, 2-hydroxy-2-methyl-1-phenylpropane-1-one, thioxanthone, diethylthioxanthone, 2-isopropylthioxanthone, 2-chlorothioxanthone, 2-methyl-1-[4-(methylthio)phenyl]-2-morpholino-propane-1-one, 2,4,6-trimethylbenzoyldiphenylphosphine oxide, bis-(2,6-dimethoxybenzoyl)-2,4,4-trimethylpentylphosphine oxide and commercially available products such as IRGACURE® 184, 369, 651, 500, 907, 1700, 1850, (Ciba Specialty Chemicals, Inc. (now owned by BASF)), LUCIRIN™ TPO (BASF), DAROCUR™ 1173 (Ciba Specialty Chemicals, Inc.), EBECRYL™ P36 (Cytec Surface Specialties, Inc.), and the like.

The photoinitiator generally is contained in the composition in a pre-mixture ingredient concentration of 0.05 wt. % or higher, preferably more than 0.1 wt. %, and more preferred, more than 2 wt. %. Generally, the amount will be about 15 wt. % or less, preferably about 10 wt. % or less and more preferably 5 wt. % or less to improve the curing speed of the liquid curable resin composition and the durability of the cured product. The amount will vary depending on the application. In considering an "effective amount", several factors can be considered including the nature of the other components in the composition, the type of material (e.g., inner or outer primary coating), the film thickness, the amount of non-yellowing which can be tolerated, the amount of surface versus through cure, whether the composition is clear or colored, and the like. The amount will be selected to provide for an optimal balance of properties for a particular application, key properties including good cure speed, non-yellowing character, and lack of harmful crystallization.

It is preferred to exclude atmospheric oxygen during the polymerization, which may be effected by $N_2$ purge, or by adding paraffin or similar wax-like substances which, at the onset of polymerization, migrate to the surface owing to lack of solubility in the polymer and form a transparent film which prevents air from entering the system. The inhibiting effect of atmospheric oxygen may also be overcome by combining accelerators (or synergists) with the photoinitiators. Examples of such accelerators or photosensitizers include secondary and/or tertiary amines, such as, dimethylethanolamine, triethanolamine, benzyldimethylamine, dimethylaminoethyl acrylate, N-phenylglycine, N-methyl-N-phenylglycine, triethylamine, diethylamine, N-methyldiethanolamine, ethanolamine, 4-dimethylaminobenzoic acid, methyl 4-dimethylamino benzoate, ethyl 4-dimethylaminobenzoate, isoamyl 4-dimethylamino benzoate, 2-ethylhexyl-4-dimethylaminobenzoate, acrylated amines, and commercially available products such as MDEA EBECRYL™ P104, 115, 7100, ADDITOL™ EHA, and ADDITOL™ EPD (Cytec Surface Specialties, Inc.).

In another embodiment, the invention provides liquid bis(acyl)phosphine photoinitiators of formula (I) in a stable form, that is, stabilized liquid bis(acyl)phosphine photoinitiators of formula (I). Bis(acyl)phosphines of formula (I) are chemically unstable compounds as they readily undergo further oxidation to the corresponding bis(acyl)phosphine oxide of formula (II).

As used herein, a "stabilized" or "stable" or "stabilized form" of liquid bis(acyl)phosphine refers to bis(acyl)phosphine that from the time of synthesis to storage to the time of use, does not undergo substantial oxidation to the corresponding phosphine oxide. For example, a stable liquid bis(acyl)phosphine comprises less than about 49 wt. % of the corresponding phosphine oxide. In an embodiment a stable liquid bis(acyl)phosphine of the invention comprises less than about 45 wt. %, or less than about 40 wt. %, or less than about 35 wt. %, or less than about 30 wt. %, or less than about 25 wt. %, or less than about 20 wt. %, or less than about 15 wt. %, or less than about 10 wt. %, or less than about 5 wt. % or less than about 2 wt. %, or less than about 1 wt. % of the corresponding phosphine oxide.

In keeping with an aspect of the invention, liquid bis(acyl)phosphines of formula (I) are stabilized using physical/mechanical techniques and/or chemical techniques. In an embodiment, liquid bis(acyl)phosphines of formula (I) are stabilized using physical or mechanical techniques. Illustrative physical or mechanical techniques include, for example, providing conditions during synthesis, storage, or use, to reduce the oxidation of the phosphine moiety to the phosphine oxide. Suitable physical or mechanical techniques include, for example, using low oxygen permeability packaging, refrigeration during shipping and storage, inert gas blanketing, and combinations thereof.

An illustrative technique of physical/mechanical stabilizing a liquid bis(acyl)phosphine of the invention is selecting a packaging having a low permeability to oxygen so as to exclude oxygen.

It is typically desirable to package liquid bis(acyl)phosphines of formula (I) in packaging to exclude oxygen thereby stabilizing the liquid bis(acyl)phosphine. Suitable low oxygen permeability packaging includes, for example, sealed metal containers such as lined steel drums or pails. In addition, polypropylene or high density polyethylene (HDPE) containers coated with vinylidene chloride copolymers and/or nylon or acrylonitrile copolymers. Typically, glass containers are undesirable since glass is prone to breakage, thus creating a possible safety hazard, but also potentially exposing the contents to atmospheric conditions (e.g., increased oxygen or humidity levels).

It is typically desirable to refrigerate liquid bis(acyl)phosphines of formula (I) during shipping and storage to reduce reactivity thereby stabilizing the liquid bis(acyl)phosphine. For example, it is desirable to maintain the temperature of liquid bis(acyl)phosphines of formula (I) below about 20° C. In an embodiment, a liquid bis(acyl)phosphine of the invention is stabilized by maintaining the temperature below about 18° C., or below about 15° C., or below about 10° C., or below about 5° C., or below about 2.5° C., or below about 1° C.

It is typically desirable to provide an inert dry atmosphere at the point of packaging and use of liquid bis(acyl)phosphines of formula (I) to exclude oxygen and moisture thereby stabilizing the liquid bis(acyl)phosphine. Suitable inert gases include, for example, nitrogen.

It is desirable to exclude moisture from stabilized liquid bis(acyl)phosphines of the invention. In an embodiment, a liquid bis(acyl)phosphine of formula (I) is stabilized as a composition comprising less than about 1.0 wt. % water. In an embodiment, a stabilized liquid bis(acyl)phosphine comprises less than about 0.75 wt. %, or less than about 0.5 wt. %, or less than about 0.25 wt. %, or less than about 0.2 wt. %, or less than about 0.15 wt. %, or less than about 0.1 wt. % water. The stabilized liquid bis(acyl)phosphine can be achieved and/or maintained, for example, by using suitable packaging during transport/storage or by inert blanketing during use of the composition.

In an embodiment, liquid bis(acyl)phosphines of formula (I) are stabilized using at least one of the described physical or mechanical techniques. In an embodiment at least two of the physical or mechanical techniques are used to stabilize liquid bis(acyl)phosphines of formula (I). In another embodiment, a combination of all the physical or mechanical techniques are used to stabilize liquid bis(acyl)phosphines of formula (I), as appropriate.

In keeping with another aspect of the invention, the liquid bis(acyl)phosphines of formula (I) are also stabilized using chemical techniques. Typically, chemical techniques for stabilizing liquid bis(acyl)phosphines of formula (I) reduce the reactivity of the phosphine moiety thereby reducing its potential for oxidation. Illustrative chemical techniques include, for example, stabilizing a liquid bis(acyl)phosphine as a mixture with one or more compounds capable of forming a mixture with the liquid bis(acyl)phosphine, wherein the mixture reduces the reactivity of the phosphine moiety, thereby providing a stabilized liquid bis(acyl)phosphine. In addition, another illustrative chemical technique is stabilizing a liquid bis(acyl)phosphine as a reaction product with a compound(s) which is capable of forming a reaction product with the liquid bis(acyl)phosphine to reduce the reactivity of the phosphine group, thereby stabilizing the liquid bis(acyl)phosphine.

In an embodiment, the invention provides a liquid bis(acyl) phosphine of formula (I) which is stabilized as a mixture with a compound selected from the group consisting of a liquid photoinitiator, a solid photoinitiator, a liquid or solid phosphite, a liquid or solid thiophosphinic acid, a liquid or solid phosphine sulfide, a liquid or solid phosphine selenide, a liquid or solid phosphine telluride, a liquid or solid phosphine halogenide, a liquid or solid iminophosphorane, and a liquid or solid dioxaphospholane.

In an embodiment, the stabilized liquid bis(acyl)phosphine of formula (I) is a mixture of liquid bis(acyl)phosphine and at least one liquid photoinitiator. In an embodiment, the at least one liquid photoinitiator is selected from the group consisting of 2,4,6-(trimethylbenzoyi ethoxy, phenyl phosphine) oxide, diethoxy acetophenone, 2-hydroxy-2-methyl-1-phenyl-propane-1-one, methyl phenylglyoxylate and acrylated benzophenone.

The stabilized mixture of liquid bis(acyl)phosphine of formula (I) and the at least one liquid photoinitiator comprises a suitable amount of the bis(acyl)phosphine. The stabilized mixture typically comprises about 25 wt. % or more, e.g., about 30 wt. % or more, about 35 wt. % or more of the liquid bis(acyl)phosphine. Alternatively, or in addition, the stabilized mixture typically comprises about 75 wt. % or less, e.g., about 70 wt. % or less, or about 65 wt. % or less of the liquid bis(acyl)phosphine. Thus, the stabilized mixture can comprise the liquid bis(acyl)phosphine in an amount bounded by any two of the above endpoints or amounts encompassed by said endpoints. For example, the stabilized mixture can comprise about 25 wt. % to about 75 wt. %, or about 30 wt. % to about 70 wt. %, or about 35 wt. % to about 65 wt. %, and the like, of the liquid bis(acyl)phosphine.

In an embodiment, the liquid bis(acyl)phosphine of formula (I) is stabilized as a eutectic mixture or eutectic system. As used herein, a eutectic system is a mixture or alloy with a melting point (i.e., eutectic temperature) lower than that of any other combination of the same components.

In an embodiment, the invention provides a liquid bis(acyl) phosphine stabilized as a eutectic mixture with at least one solid photoinitiator.

In an embodiment, the stabilized liquid bis(acyl)phosphine of formula (I) is a mixture of liquid bis(acyl)phosphine and at least one solid photoinitiator. In an embodiment, the at least one solid photoinitiator is selected from the group consisting of 4-methyl benzophenone, p-phenyl benzophenone, 4,4'-bis (dimethylamino)benzophenone, 4-benzoyl-4'-methyl diphenylsulfide, 4,4'-(tetraethyldiamino)benzophenone, 4,4'-(tetraethyldiamino)benzophenone, benzophenone, 2-hydroxy- 1-{4-[4-(2-hydroxy-2-methyl-propionyl)-benzyl]-phenyl}-2-methyl-propan-1-one, 1-hydroxycyclohexyl phenyl ketone, 2,2-dimethoxy-2-phenylacetophenone, 4-(2-hydroxyethoxy)phenyl-(2-propyl)ketone, camphorquinone and 2,4,6-trimethylbenzophenone.

The stabilized mixture of liquid bis(acyl)phosphine of formula (I) and the at least one solid photoinitiator comprises a suitable amount of the liquid bis(acyl)phosphine. The stabilized mixture typically comprises about 25 wt. % or more, e.g., about 30 wt. % or more, about 35 wt. % or more of the liquid bis(acyl)phosphine. Alternatively, or in addition, the stabilized mixture typically comprises about 75 wt. % or less, e.g., about 70 wt. % or less, or about 65 wt. % or less of the liquid bis(acyl)phosphine. Thus, the stabilized mixture can comprise the liquid bis(acyl)phosphine in an amount bounded by any two of the above endpoints or amounts encompassed by said endpoints. For example, the stabilized mixture can comprise about 25 wt. % to about 75 wt. %, or about 30 wt. % to about 70 wt %, or about 35 wt. % to about 65 wt. %, and the like, of the liquid bis(acyl)phosphine.

In an embodiment of the invention, the stabilized liquid bis(acyl)phosphine of formula (I) is a mixture of liquid bis (acyl)phosphine and one or more liquid or solid phosphite, a liquid or solid thiophosphinic acid, a liquid or solid phosphine sulfide, a liquid or solid phosphine selenide, a liquid or solid phosphine telluride, a liquid or solid phosphine halogenide, a liquid or solid iminophosphorane, and a liquid or solid dioxaphospholane. Not wishing to be bound by any particular theory, it is believed that the one or more liquid or solid phosphite, a liquid or solid thiophosphinic acid, a liquid or solid phosphine sulfide, a liquid or solid phosphine selenide, a liquid or solid phosphine telluride, a liquid or solid phosphine halogenide, a liquid or solid iminophosphorane, and a liquid or solid dioxaphospholane acts as an antioxidant for the liquid bis(acyl)phosphine to reduce oxidation of the phosphine.

The stabilized liquid bis(acyl)phosphine can comprise any suitable amount of the one or more compounds capable of reducing the reactivity of the phosphine moiety. In an embodiment, the liquid bis(acyl)phosphine is stabilized as about a 1:1 mixture of phosphine/stabilizing compound. In another embodiment, the mixture is about a 2:1 mixture, or about a 3:1 mixture, or about a 4:1 mixture of phosphine/ stabilizing compound.

In an embodiment, the stabilized liquid bis(acyl)phosphine of formula (I) is a mixture of bis(acyl)phosphine and at least one liquid or solid phosphite of formula (III):

$$R^1O-P-OR^3, \atop OR^2 \qquad (III)$$

wherein each of $R^1$, $R^2$ and $R^3$ is independently selected from the group consisting of a $C_1$-$C_{12}$ alkyl or phenyl.

In an embodiment, each of $R^1$, $R^2$ and $R^3$ of formula (III) is independently selected from an alkylphenyl group.

In an embodiment, the liquid or solid phosphite of formula (III) is selected from the group consisting of tris(nonylphenyl)phosphite, tributyl phosphite, or mixtures thereof. An illustrative solid phosphite is triphenyl phosphite, which has a melting point of 22-24° C.

The stabilized liquid bis(acyl)phosphine can comprise any suitable amount of the phosphite. In an embodiment, the bis(acyl)phosphine is stabilized as about a 1:1 mixture of phosphine/phosphite. In another embodiment, the mixture is about a 2:1 mixture, or about a 3:1 mixture, or about a 4:1 mixture of phosphine/phosphite.

In an embodiment, the stabilized liquid bis(acyl)phosphine of formula (I) is a mixture of bis(acyl)phosphine and at least one liquid or solid thiophosphinic acid of formula (IV):

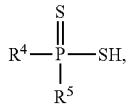

(IV)

wherein each of $R^4$ and $R^5$ is independently selected from the group consisting of an alkyl group, an aryl group, an acyl group, and a heteroaryl group, wherein each of $R^4$ and $R^5$ is optionally substituted.

In another embodiment, the stabilized liquid bis(acyl)phosphine of formula (I) is a mixture of bis(acyl)phosphine and at least one liquid or solid compound of the formula:

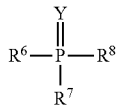

wherein Y is selected from the group of sulfur, selenium, and tellurium, and wherein each of $R^6$, $R^7$, and $R^8$ is independently selected from the group consisting of an alkyl group, an aryl group, an acyl group, and a heteroaryl group, wherein each of $R^6$, $R^7$, and $R^8$ is optionally substituted.

In an embodiment, the stabilized liquid bis(acyl)phosphine of formula (I) is a mixture of bis(acyl)phosphine and at least one liquid or solid phosphine sulfide of formula (V):

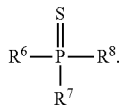

(V)

In an embodiment, the stabilized liquid bis(acyl)phosphine of formula (I) is a mixture of bis(acyl)phosphine and at least one liquid or solid selenide of formula (VI):

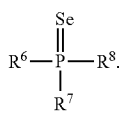

(VI)

In an embodiment, the stabilized liquid bis(acyl)phosphine of formula (I) is a mixture of bis(acyl)phosphine and at least one liquid or solid telluride of formula (VII):

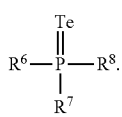

(VII)

In an embodiment, the stabilized liquid bis(acyl)phosphine of formula (I) is a mixture of bis(acyl)phosphine and at least one liquid or solid halogenide of formula (VIII):

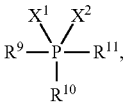

(VIII)

wherein each of $R^9$, $R^{10}$, and $R^{11}$ is independently selected from the group consisting of an alkyl group, an aryl group, an acyl group, and a heteroaryl group, wherein each of $X^1$ and $X^2$ is independently a halogen, and wherein each of $R^9$, $R^{10}$, and $R^{11}$ is optionally substituted.

In an embodiment, the stabilized liquid bis(acyl)phosphine of formula (I) is a mixture of bis(acyl)phosphine and at least one liquid or solid iminophosphorane of formula (IX):

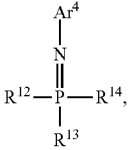

(IX)

wherein each of $R^{12}$, $R^{13}$, and $R^{14}$ is independently selected from the group consisting of an alkyl group, an aryl group, an acyl group, and a heteroaryl group, wherein $Ar^4$ is an aryl group, and wherein each of $R^{12}$, $R^{13}$, $R^{14}$, and $Ar^4$ is optionally substituted.

In an embodiment, the stabilized liquid bis(acyl)phosphine of formula (I) is a mixture of bis(acyl)phosphine and at least one liquid or solid dioxaphospholane of formula (X).

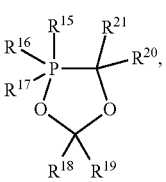

(X)

wherein each of $R^{15}$, $R^{16}$, $R^{17}$, $R^{18}$, $R^{19}$, $R^{20}$, and $R^{21}$ is independently selected from the group consisting of an alkyl group, an aryl group, an acyl group, and a heteroaryl group and wherein each of $R^{15}$, $R^{16}$, $R^{17}$, $R^{18}$, $R^{19}$, $R^{20}$, and $R^{21}$ is optionally substituted.

In an embodiment, the invention provides a liquid bis(acyl)phosphine of formula (I) which is stabilized as a reaction product with a compound selected from the group consisting of a metal, dodecylsuccinic anhydride, a urea compound, a Lewis acid and a catechol compound.

As described herein, "metal" refers to a chemical element that is a good conductor of both electricity and heat and forms cations and ionic bonds with non-metals. In addition, metal atoms readily lose electrons to form positive ions (cations). Those ions are surrounded by delocalized electrons, which are responsible for the conductivity. The solid thus produced is held by electrostatic interactions between the ions and the electron cloud, which are called metallic bonds.

In accordance with an embodiment of the invention, a liquid bis(acyl)phosphine of formula (I) can be stabilized as coordination complex to a metal. A coordination complex or metal complex, is a structure consisting of a central atom or ion (usually metallic), bonded to a surrounding array of molecules or anions (ligands, complexing agents). The atom within a ligand that is directly bonded to the central atom or ion is called the donor atom. Polydentate (multiple bonded) ligands can form a chelate complex. A ligand donates at least one pair of electrons to the central atom/ion. Compounds that contain a coordination complex are called coordination compounds. The central atom or ion, together with all ligands form the coordination sphere. Coordination refers to the "coordinate covalent bonds" (dipolar bonds) between the ligands and the central atom.

A dipolar bond, also known as coordinate link, coordinate covalent bond, dative bond, or semipolar bond, is a description of covalent bonding between two atoms in which both electrons shared in the bond come from the same atom. Once such a bond has been formed, its strength and description is no different from that of other polar covalent bonds. Dipolar bonds occur when a Lewis base (an electron pair donor or giver) donates a pair of electrons to a Lewis acid (an electron pair acceptor) to give a so-called adduct. The process of forming a dipolar bond is called coordination. The electron donor acquires a positive formal charge, while the electron acceptor acquires a negative formal charge.

Dipolar bonding is popularly used to describe coordination complexes, especially involving metal ions. In such complexes, several Lewis bases "donate" their "free" pairs of electrons to an otherwise naked metal cation, which acts as a Lewis acid and "accepts" the electrons. Dipolar bonds form and the resulting compound is called a coordination complex, and the electron donors are called ligands. A more useful description of bonding in coordination compounds is provided by Ligand Field Theory, which embraces molecular orbitals as a description of bonding in such polyatomic compounds. Many chemical compounds can serve as ligands. Often these contain oxygen, sulfur, nitrogen and halide ions. The most common ligand is water ($H_2O$), which forms coordination complexes with metal ions (like the hexaaquacopper (II) ion, $[Cu(H_2O)_6]^{2+}$). Ammonia ($NH_3$) is a common ligand. So are some anions, especially fluoride ($F^-$), chloride ($Cl^-$) and cyanide ($CN^-$).

Aspects of metal-phosphine chemistry are disclosed in, for example, "Phosphines and Metal Phosphine Complexes: Relationship of Chemistry to Anticancer and Other Biological Activity", Berners-Price, S. J., and Sadler, P. J.; in *Structure and Bonding*, 70, (1988), pp 28-97; and in "Concepts of Inorganic Photochemistry", eds, Adamson, A. W., and Fleischauer, (1984), pp. 299-330; and in "Chelating Agents" in *Kirk-Othmer Encyclopedia of Chemical Technology*, 4th edition, v5, (1993) pp. 764-792, each of which is incorporated herein by reference in their entirety.

Not wishing to be bound to a particular theory, it is believed that the metal complexes reduce the reactivity of the phosphine moiety towards oxidation.

In an embodiment the metal is a transition metal.

In another embodiment the metal is selected from the group consisting of vanadium (V), iron (Fe), Indium (In), thorium (Th), mercury (Hg), copper (Cu), nickel (Ni), yttrium (Y), lead (Pb), zinc (Zn), cadmium (Cd), cobalt (Co), manganese (Mn), calcium (Ca), magnesium (Mg), strontium (Sr), barium (Ba), zirconium (Zr), titanium (Ti), chromium (Cr), rubidium (Rb), molybdenum (Mo), ruthenium (Ru), palladium (Pd), silver (Ag), cadmium (Cd), tin (Sn), antimony (Sb), barium (Ba), tungsten (W), platinum (Pt), gold (Au), bismuth (Bi) and beryllium (Be).

In an embodiment, the stabilized liquid bis(acyl)phosphine has the formula (XI):

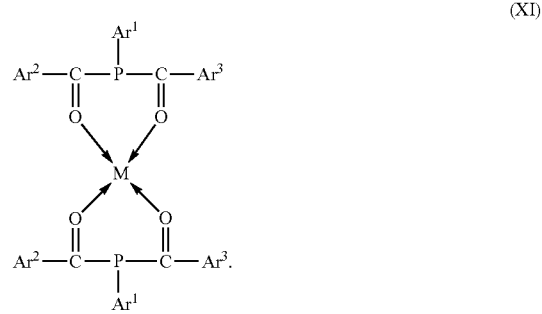

(XI)

In an embodiment, the stabilized liquid bis(acyl)phosphine has the formula (XII):

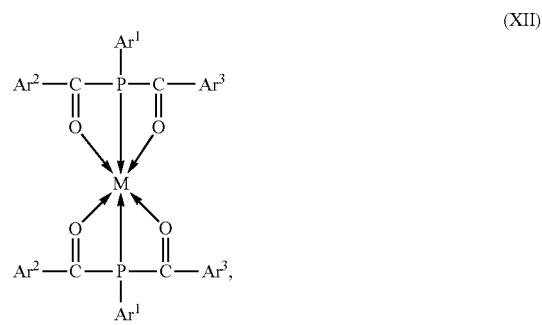

(XII)

wherein each of $Ar^1$, $Ar^2$ and $Ar^3$ of each of compound (XI) and compound (XII) have the meaning as described for a compound of formula (I), and M is a metal or metal ion as described herein.

In an embodiment, the Lewis acid is selected from the group consisting of supramolecular polymers, imidazole derivatives and guanidine derivatives.

A Lewis acid is a chemical substance that can accept a pair of electrons from a Lewis base acting as an electron-pair donor to form an adduct.

A supramolecular polymer is a polymer whose monomer repeat units are held together by noncovalent bonds. Noncovalent forces that hold supramolecular polymers together include coordination, π-π interactions and hydrogen bonding. One system that has been demonstrated uses quadruple hydrogen bonds to form supramolecular polymers. Functionalization of polymers with the quadruple hydrogen bonding unit from the Meijer group introduces reversible cross-links and a virtual increase in the polymer's molecular weight. In general, polymers with a higher molecular weight possess better material properties.

Examples of suitable supramolecular polymers are known to the skilled artisan.

Examples of suitable imidazole derivatives are known to the skilled artisan.

Examples of suitable guanidine derivatives are known to the skilled artisan.

In an embodiment, the invention provides a liquid bis(acyl) phosphine which is stabilized as a mixture with a catechol compound (I.e., α,β-dihydroxybenzene compounds). Not wishing to be bound by a particular theory, the catechol compound acts an antioxidant to stabilize the bis(acyl)phosphine. Illustrative catechol compounds include, for example, 4-tert-butyl catechol, 3,5-di-tert-butyl catechol, 3,4-dihydroxyphenyl ethanol, 3,4-dihydroxybenzopheone and 6,7-dihydroxycoumarin. In an embodiment, the catechol compound is 4-tert-butyl catechol. In another embodiment, the catechol compound is 3,5-di-tert-butyl catechol. In keeping with an aspect of the invention, in some embodiments the catechol compound also is photoactive, thereby increasing the efficiency of the photoinitiation process. Moreover, in some embodiments, the stabilized mixture of bis(acyl)phosphine with the catechol compound is a eutectic mixture.

In accordance with an embodiment of the invention, liquid bis(acyl)phosphines can be stabilized by noncovalent interactions with other compounds such as, for example, hydrogen bonding or ionic bonding.

Noncovalent bonding typically refers to a variety of interactions that are not covalent in nature between molecules or parts of molecules that provide force to hold the molecules or parts of molecules together, usually in a specific orientation or conformation. The terms "noncovalent bonding," "noncovalent interactions," and "noncovalent forces" all refer to these forces as a whole without specifying or distinguishing which specific forces are involved: noncovalent interactions often involve several of these forces working in concert.

A noncovalent bond is a type of chemical bond, typically between macromolecules, that does not involve the sharing of pairs of electrons, but rather involves more dispersed variations of electromagnetic interactions. The noncovalent bond is the dominant type of bond between supramolecules in supramolecular chemistry. Noncovalent bonds are critical in maintaining the three-dimensional structure of large molecules, such as proteins and nucleic acids, and are involved in many biological processes in which large molecules bind specifically but transiently to one another. Common types of non-covalent interactions include, for example, hydrogen bonds, ionic bonds, van der Waals forces (i.e., "London dispersion forces", and dipole-dipole bonds) and hydrophobic interactions. The noncovalent interactions hold together the two strands DNA in the double helix, stabilize secondary and tertiary structures of proteins and enable enzyme-substrate binding and antibody-antigen association.

Hydrogen bonding is the attractive interaction of a hydrogen atom with an electronegative atom, such as nitrogen, oxygen or fluorine. The hydrogen must be covalently bonded to another electronegative atom to create the bond. These bonds can occur between molecules (intermolecularly), or within different parts of a single molecule (intramolecularly).

An ionic bond is a type of chemical bond that involves a metal and a nonmetal ion (or polyatomic ions such as ammonium) through electrostatic attraction (i.e., it is a bond formed by the attraction between two oppositely charged ions). The metal donates one or more electrons, forming a positively charged ion or cation with a stable electron configuration. These electrons then enter the non metal, causing it to form a negatively charged ion or anion which also has a stable electron configuration. The electrostatic attraction between the oppositely charged ions causes them to come together and form a bond.

In an embodiment, the stabilized liquid bis(acyl)phosphine has the formula (XIII):

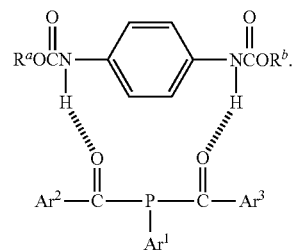

(XIII)

In an embodiment, the stabilized liquid bis(acyl)phosphine has the formula (XIV):

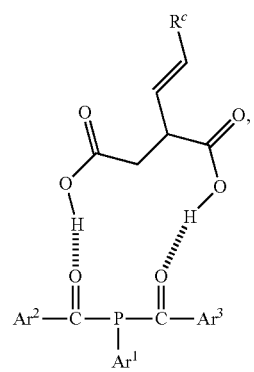

(XIV)

wherein each of $Ar^1$, $Ar^2$ and $Ar^3$ of each of compound (XIII) and compound (XIV) have the meaning as described for a compound of formula (I), and each of $R^a$, $R^b$, and $R^c$ are selected from the group consisting of hydrogen, an alkyl group and a substituted alkyl group, wherein the alkyl group and substituted alkyl group are optionally substituted. Suitable alkyl groups include, for example, $C_1$-$C_{18}$ alkyl groups (e.g., $C_1$-$C_{12}$ alkyl groups, $C_1$-$C_9$ alkyl groups, $C_1$-$C_6$ alkyl groups and $C_1$-$C_3$ alkyl groups).

In keeping with an aspect of the invention, the liquid bis (acyl)phosphines of formula (XIII) and (XIV) are stabilized by hydrogen bonding.

In another embodiment, the invention provides a radiation curable composition comprising a stabilized liquid bis(acyl) phosphine. In keeping with the invention, the radiation curable composition can be any radiation curable composition as described herein including but not limited to a radiation curable optical fiber coating composition, and a coating composition capable of radiation cure on concrete and a coating composition capable of radiation cure on metal. Further, the radiation curable compositions of the invention comprise at least one of the stabilized liquid bis(acyl)phosphines described herein. In an embodiment, the radiation curable composition comprises or consists of stabilized liquid bis(2, 4,6-trimethylbenzoyl)phosphine.

The radiation curable composition comprises a suitable amount of at least one stabilized liquid bis(acyl)phosphine. The radiation curable compositions typically comprise about 5 wt. % of a stabilized liquid bis(acyl)phosphine. In an embodiment, the radiation curable composition comprises about 4 wt. %, or about 3 wt. %, or about 2.5 wt. %, or about 2 wt. %, or about 1 wt. %, or about 0.5 wt. %, or about 0.1 wt. % of a stabilized liquid bis(acyl)phosphine.

The following examples further illustrate the invention but, of course, should not be construed as in any way limiting its scope.

EXAMPLES

Cure Speed FTIR Test (% RAU). The relative cure rates for ultraviolet cured coatings can be determined using FTIR transmission techniques. The method is applicable to coating systems that cure by loss of double bonds when exposed to ultraviolet light.

Infrared spectrometry is a well known and any infrared spectrometer can be utilized to obtain the infrared spectrum. For example, a Nicolet model 860 Fourier transform infrared (FTIR) spectrophotometer or equivalent can be used with the following parameters: TGS detector, 4 cm$^{-1}$ resolution and ten scans are co-added for each spectrum.

A Mercury UV lamp, 100 W, Oriel Corp. #6281 or equivalent is used. Alternative UV lamp systems capable of producing controlled short pulses of radiation may be substituted.

Sample Preparation, A Teflon spacer is placed onto the surface of a clean NaCl transmission window. By using a precision microliter pipette, a small drop of thoroughly mixed coating is placed in the center of the NaCl disc. A second NaCl disc is placed carefully on top of the drop of coating such that the coating spreads evenly to the edge of the spacer and such that no air bubbles are present in the coating.

Instrument Set-up/Standardization. The UV lamp is turned on, then the FTIR is turned on. A background spectrum is collected with no sample in the IR beam path.

Procedure for Analyzing Samples. For a first analysis of a coating system a standard procedure is followed to ensure that the coating thickness is constant for any one coating system. A 50 micron spacer is used for achieving a constant thickness. Therefore, the net absorbance of the unsaturation band from the peak minimum to the peak maximum is measured. The peak maximum should be in the 1.0 to 1.2 Å range. The net absorbance will depend on the peak minimum. For coatings based on acrylate chemistry, the acrylate unsaturation band at 810 cm$^{-1}$ and a baseline at the minimum near 795 cm$^{-1}$ is used. This step is repeated three times and the average of the three absorbance values is taken as the net absorbance. This averaged value is used as a target absorbance for all future analyses of that particular coating system. This value is likely to differ for each coating system due to the differences in unsaturation content. The coating thickness is then adjusted by tightening the demountable cell holder screws until the net absorbance of the unsaturation band is within ±.0.05 Å of the above described averaged value for the net absorbance. Spectra are collected, one right after another, until the net absorbance value stabilizes (the coating may take a few minutes to reach equilibrium).

Then, an infrared spectrum of the uncured, liquid sample and an infrared spectrum of the cured sample are obtained by varying the exposure times between 0.05 and 5 seconds. Exposure times may vary depending on the coating system, for example, fast curing coating systems require shorter exposure times.

The net peak area of the acrylate unsaturation absorbance for the uncured liquid sample is measured. For most acrylate-based coatings, the absorbance at about 810 cm$^{-1}$ should be used. However, if the coating contains a siloxane or other component which absorbs strongly at or near 810 an alternative acrylate absorbance peak can be used. The absorbances at about 1410 cm$^{-1}$ and about 1635 cm$^{-1}$ have been found to be satisfactory. The net peak area can be measured using the well known baseline technique in which a baseline is drawn tangent to absorbance minima on either side of the peak. The area above the baseline and under the peak is the net peak area.

For some coating systems, the loss of unsaturation absorbance due to UV exposure results in a spectral valley rather than a flat baseline. For such samples, it is desirable to perform spectral subtraction of the final exposure from each of the previous spectra using a subtraction factor of 1.00. The subtracted spectra should then be used for the area measurements.

The percent reacted acrylate unsaturation (% RAU) for each exposure is calculated using the following equation: % RAU=[A(liq)−A(exposed)]/A(liq)×100, where: A(liq) is the net area of the 810 cm$^{-1}$ band for the liquid coating; and A(exposed) is the net area of the 810 cm$^{-1}$ band after exposure.

The average % RAU is determined for the triplicate analyses for each time exposure.

Example 1 and Comparative Example A

This example illustrates a radiation curable, optical fiber coating composition of the invention comprising a liquid bis(acyl)phosphine of formula (I) and a free-radical polymerizable component.

The radiation curable, optical fiber coating composition of Example 1 contains: 60 wt. % of an oligomer containing the components listed in Table 1; a monomer blend containing SR 504D, SR 339A, SR 349D and vinyl caprolactam; 0.10 wt. % TINUVIN™ 123 as a light stabilizer; 0.60 wt. % IRGANOX™ 1035 as an antioxidant; and 1.00 wt. % of γ-mercaptopropyl trimethoxy silane as an adhesion promoter. The curable coating composition of Example 1 also contains 2.00 wt % of liquid LMBAPO as a photoinitiator.

The radiation curable, optical fiber coating composition of Comparative Example A is identical to the coating composition of Example 1, but comprises 2% IRGACURE® 819 BAPO as a solid photoinitiator instead of the liquid. LMBAPO.

After preparing the radiation curable, optical fiber coating compositions, the % RAU of each coating composition is measured as described herein. The results are depicted in Table 1.

TABLE 1

| Components | Comparative Ex. A | Ex. 1 |
|---|---|---|
| ACCLAIM ™ polyol 4200 | 54.68 | 54.68 |
| acrylic acid, 99% | 0.01 | 0.01 |
| BHT | 0.09 | 0.09 |
| MONDUR ™ TDS | 3.79 | 3.79 |
| dibutyltin dilaurate | 0.03 | 0.03 |
| 2-HEA | 1.85 | 1.85 |
| Total Oligomer wt. % | 60.00 | 60.00 |
| SR 504D | 18.20 | 18.20 |
| SR 339 A | 12.15 | 12.15 |
| SR 349D | 2.00 | 2.00 |
| vinyl caprolactam | 3.50 | 3.50 |
| TINUVIN ™ 123 | 0.10 | 0.10 |
| IRGANOX ™ 1035 | 0.60 | 0.60 |
| γ-mercaptopropyl trimethoxy silane | 1.00 | 1.00 |
| IRGACURE ® 819 BAPO | 2.00 | |
| LMBAPO | | 2.00 |
| % RAU | | |
| % RAU (2.2 mJ/cm$^2$) | 54.5 | 47.7 |
| % RAU (4.4 mJ/cm$^2$) | 85.8 | 81.1 |
| % RAU (11 mJ/cm$^2$) | 92.6 | 90.9 |

As set forth in Table 1, the results of the % RAU measurement indicate that the radiation curable, optical fiber coating composition of Example 1 containing a liquid photoinitiator offers comparable and satisfactory cure speed, as indicated by the % RAU, when compared to the coating composition of Comparative Example A containing a solid photoinitiator.

Example 2

This example illustrates a process of preparing liquid bis-(2,4,6-trimethylbenzoyl)-phenylphosphine in accordance with the invention.

Under an inert atmosphere and with exclusion of moisture a dispersion of sodium (11.5 g, 0.50 mol) in toluene (100 mL) is produced by stirring with a high speed turbine stirrer with 11,000 rpm at 105° C., resulting in sodium with a main particle size of less than 50 µm. The mixture is cooled to 30-35° C. without stirring. Then the turbine stirrer is started again and chlorobenzene (2.8 g, 0.025 mol) is added dropwise and the contents of the flask warms to 45-50° C. The resulting black suspension is heated to 100° C. and P,P-dichlorophenylphosphine (19.7 g, 0.11 mol) is added dropwise at this temperature with exothermic behavior. After the addition of ¼ of the whole amount of P,P-dichlorophenylphosphine the reaction stops to develop heat. At this point n-butanol (0.05 mL) is added and the exothermic reaction starts again. All the rest of the addition of P,P-dichlorophenylphosphine stays exothermic. The resulting green suspension is stirred at 100-110° C. for 30 minutes. The mixture is cooled to 75° C. and 2,4,6-trimethylbenzoylchloride (43.8 g, 0.24 mol) is added dropwise over a period of 30 minutes at this temperature. An exothermic reaction is observable. To the brown suspension is added toluene (200 mL) and the mixture is stirred for 60 minutes at 70-85° C. The mixture is hydrolyzed with water (150 mL) and the phases are separated. The product phase is analyzed by $^{31}$P-NMR. This shows the desired bis-(2,4,6-trimethylbenzoyl)-phenylphosphine.

All references, including publications, patent applications and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A radiation curable composition for optical fiber comprising a liquid bis(acyl)phosphine of formula (I):

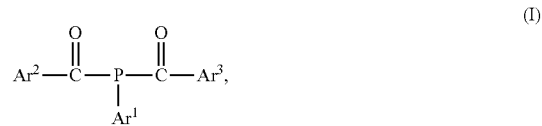

and at least one free-radical polymerizable component;
wherein each of $Ar^1$, $Ar^2$ and $Ar^3$ is independently selected from the group consisting of a phenyl group, a methylphenyl group, an ethylphenyl group, a dimethylphenyl group, a trialkylphenyl group, an isopropylphenyl group, a tert-butyl phenyl group, a methoxy phenyl group, a dimethoxyphenyl group, an ethoxy phenyl group, a diethoxy phenyl group, an isopropoxy phenyl group, a thiomethoxy phenyl group, a naphthyl group, a thiophenyl group and a pyridyl group; and
wherein said liquid bis(acyl)phosphine of formula (I) is liquid at 20° C. and is stabilized as a composition comprising less than about 1.0 wt. % water.

2. The radiation curable composition of claim 1, wherein each of $Ar^1$, $Ar^2$ and $Ar^3$ is independently a trialkylphenyl group and wherein the trialkylphenyl group is a 2,4,6-trimethylphenyl group.

3. The radiation curable composition of claim 1, wherein the phosphine is bis(2,4,6-trimethylbenzoyl)phenylphosphine wherein $Ar^1$ is a phenyl group and each of $Ar^2$ and $Ar^3$ is a 2,4,6-trimethylphenyl group.

4. An optical fiber coating composition, which is the radiation curable composition of claim 1, wherein the optical fiber coating composition is selected from the group consisting of a primary coating, a secondary coating, an ink coating, an upjacketing coating, a buffer coating and a matrix coating.

5. The radiation curable composition of claim 1, further comprising a liquid bis(acyl)phosphine oxide of formula (II):

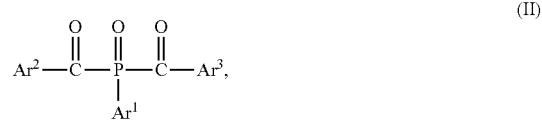

wherein each of $Ar^1$, $Ar^2$ and $Ar^3$ is independently a selected from the group consisting of a phenyl group, a methylphenyl group, an ethylphenyl group, a dimethylphenyl group, a trialkylphenyl group, an isopropylphenyl group, a tert-butyl phenyl group, a methoxy phenyl group, a dimethoxyphenyl group, an ethoxy phenyl group, a diethoxy phenyl group, an isopropoxy a phenyl group, a thiomethoxy phenyl group, a naphthyl group, a thiophenyl group and a pyridyl group.

6. The radiation curable composition of claim 5, wherein each of $Ar^1$, $Ar^2$ and $Ar^3$ is independently a trialkylphenyl group and the trimethylphenyl group is a 2,4,6-trimethylphenyl group.

7. The radiation curable composition of claim 5, wherein the phosphine oxide is bis(2,4,6-trimethylbenzoyl)phenylphosphine oxide, wherein $Ar^1$ is a phenyl group and each of $Ar^2$ and $Ar^3$ is a 2,4,6-trimethylphenyl group.

8. A radiation curable composition selected from the group consisting of an optical fiber coating composition and a coating composition capable of radiation cure on concrete and a coating composition capable of radiation cure on metal comprising at least one free-radical polymerizable component and a combination of at least two photoinitiators wherein at least one photoinitiator is liquid bis(2,4,6-trimethylbenzoyl) phenylphosphine and at least one photoinitiator is bis(2,4,6-trimethylbenzoyl)phenylphosphine oxide.

9. The radiation curable composition of claim 8, wherein the combination of bis(acyl)phosphine and bis(acyl)phosphine oxide are liquid at a temperature of about 15° C. or greater.

10. The radiation curable composition of claim 9, wherein liquid bis(2,4,6-trimethylbenzoyl)phenylphosphine and bis(2,4,6-trimethylbenzoyl)phenylphosphine oxide are present in a ratio of about 1:1 as measured by HPLC.

11. The radiation curable composition of claim 1, wherein the composition is curable by UV light generated by a conventional UV light source.

12. The radiation curable composition of claim 1, wherein the composition is curable by light generated by a LED light source.

13. The radiation curable composition for optical fiber of claim 1 wherein said liquid bis(acyl)phosphine of formula (I) is stabilized as a composition comprising less than about 0.75 wt. % water.

14. The radiation curable composition for optical fiber of claim 1 wherein said liquid bis(acyl)phosphine of formula (I) is stabilized as a composition comprising less than about 0.5 wt. % water.

15. The radiation curable composition for optical fiber of claim 1 wherein said liquid bis(acyl)phosphine of formula (I) is stabilized as a composition comprising less than about 0.25 wt. % water.

16. The radiation curable composition for optical fiber of claim 1 wherein said liquid bis(acyl)phosphine of formula (I) is stabilized as a composition comprising less than about 0.2 wt. % water.

17. The radiation curable composition for optical fiber of claim 1 wherein said liquid bis(acyl)phosphine of formula (I) is stabilized as a composition comprising less than about 0.15 wt. % water.

18. The radiation curable composition for optical fiber of claim 1 wherein said liquid bis(acyl)phosphine of formula (I) is stabilized as a composition comprising less than about 0.1 wt. % water.

* * * * *